(12) United States Patent
Balakin

(10) Patent No.: US 8,309,941 B2
(45) Date of Patent: *Nov. 13, 2012

(54) CHARGED PARTICLE CANCER THERAPY AND PATIENT BREATH MONITORING METHOD AND APPARATUS

(76) Inventor: Vladimir Balakin, Protvino (RU)

(*) Notice: Subject to any disclaimer, the term of this patent is extended or adjusted under 35 U.S.C. 154(b) by 392 days.

This patent is subject to a terminal disclaimer.

(21) Appl. No.: 12/561,675

(22) Filed: Sep. 17, 2009

(65) Prior Publication Data

US 2010/0008466 A1 Jan. 14, 2010

Related U.S. Application Data

(63) Continuation-in-part of application No. 12/425,683, filed on Apr. 17, 2009, now Pat. No. 7,939,809.

(60) Provisional application No. 61/055,395, filed on May 22, 2008, provisional application No. 61/137,574, filed on Aug. 1, 2008, provisional application No. 61/192,245, filed on Sep. 17, 2008, provisional application No. 61/055,409, filed on May 22, 2008, provisional application No. 61/203,308, filed on Dec. 22, 2008, provisional application No. 61/188,407, filed on Aug. 11, 2008, provisional application No. 61/188,406, filed on Aug. 11, 2008, provisional application No. 61/189,815, filed on Aug. 25, 2008, provisional application No. 61/201,731, filed on Dec. 15, 2008, provisional application No. 61/205,362, filed on Jan. 21, 2009, provisional application No. 61/134,717, filed on Jul. 14, 2008, provisional application No. 61/134,707, filed on Jul. 14, 2008, provisional application No. 61/201,732, filed on Dec. 15, 2008, provisional application No. 61/198,509, filed on Nov. 7, 2008, provisional application No. 61/134,718, filed on Jul. 14, 2008, provisional (Continued)

(30) Foreign Application Priority Data

Mar. 4, 2009 (WO) ................ PCT/RU2009/000015

(51) Int. Cl.
*H05H 7/10* (2006.01)
(52) U.S. Cl. ...................... 250/492.3; 315/507; 315/503
(58) Field of Classification Search ................ 250/492.1
See application file for complete search history.

(56) References Cited

U.S. PATENT DOCUMENTS 2,306,875 A 12/1942 Fremlin
(Continued)

FOREIGN PATENT DOCUMENTS

EP 1683545 A2 7/2006
(Continued)

OTHER PUBLICATIONS

Adams, "Electrostatic cylinder lenses II: Three Element Einzel Lenses", Journal, Feb. 1, 1972, pp. 150-155, XP002554355, vol. 5 No. 2, Journal of Physics E.

(Continued)

*Primary Examiner* — Jack Berman
*Assistant Examiner* — Eliza Osenbaugh-Stewart
(74) *Attorney, Agent, or Firm* — Kevin Hazen

(57) ABSTRACT

The invention comprises a patient respiration monitoring and/or control method and apparatus used in conjunction with multi-axis charged particle or proton beam radiation therapy of cancerous tumors. The respiration monitoring system uses thermal and/or force sensors to determine where a patient is in a respiration cycle in combination with a feedback signal control delivered to the patient to inform the patient when breath control is required. The resulting breath control is timed with charged particle delivery to the tumor to enhance accuracy, precision, and/or efficiency of tumor treatment.

3 Claims, 19 Drawing Sheets

Related U.S. Application Data

(60) application No. 61/190,613, filed on Sep. 2, 2008, provisional application No. 61/191,043, filed on Sep. 8, 2008, provisional application No. 61/192,237, filed on Sep. 17, 2008, provisional application No. 61/201,728, filed on Dec. 15, 2008, provisional application No. 61/190,546, filed on Sep. 2, 2008, provisional application No. 61/189,017, filed on Aug. 15, 2008, provisional application No. 61/198,248, filed on Nov. 5, 2008, provisional application No. 61/198,508, filed on Nov. 7, 2008, provisional application No. 61/197,971, filed on Nov. 3, 2008, provisional application No. 61/199,405, filed on Nov. 17, 2008, provisional application No. 61/199,403, filed on Nov. 17, 2008, provisional application No. 61/199,404, filed on Nov. 17, 2008, provisional application No. 61/209,529, filed on Mar. 9, 2009, provisional application No. 61/208,182, filed on Feb. 23, 2009, provisional application No. 61/208,971, filed on Mar. 3, 2009.

U.S. PATENT DOCUMENTS

| Patent No. | | Date | Inventor |
|---|---|---|---|
| 2,533,688 | A | 12/1950 | Quam |
| 2,613,726 | A | 10/1952 | Veil Paatero Yrjo |
| 2,790,902 | A | 4/1957 | Wright |
| 3,128,405 | A | 4/1964 | Lambertson |
| 3,412,337 | A | 11/1968 | Lothrop |
| 3,582,650 | A | 6/1971 | Avery |
| 3,585,386 | A | 6/1971 | Horton |
| 3,655,968 | A | 4/1972 | Moore |
| 3,867,705 | A | 2/1975 | Hudson |
| 3,882,339 | A | 5/1975 | Rate |
| 3,906,280 | A | 9/1975 | Andelfinger |
| 4,002,912 | A | 1/1977 | Johnson |
| 4,344,011 | A | 8/1982 | Hayashi |
| 4,607,380 | A | 10/1986 | Oliver |
| 4,622,687 | A | 11/1986 | Whitaker |
| 4,705,955 | A | 11/1987 | Mileikowsky |
| 4,726,046 | A | 2/1988 | Nunan |
| 4,730,353 | A | 3/1988 | Ono |
| 4,868,844 | A | 9/1989 | Nunan |
| 4,870,287 | A | 9/1989 | Cole |
| 4,992,746 | A | 2/1991 | Martin |
| 4,998,258 | A | 3/1991 | Ikeda |
| 5,017,789 | A | 5/1991 | Young |
| 5,017,882 | A | 5/1991 | Finlan |
| 5,039,867 | A | 8/1991 | Nishihara |
| 5,073,913 | A | 12/1991 | Martin |
| 5,098,158 | A | 3/1992 | Palarski |
| 5,101,169 | A | 3/1992 | Gomei |
| 5,117,194 | A | 5/1992 | Nakanishi |
| 5,168,241 | A | 12/1992 | Hirota |
| 5,168,514 | A | 12/1992 | Horton |
| 5,177,448 | A | 1/1993 | Ikeguchi |
| 5,216,377 | A | 6/1993 | Nakata |
| 5,260,581 | A | 11/1993 | Lesyna |
| 5,285,166 | A | 2/1994 | Hiramoto |
| 5,349,198 | A | 9/1994 | Takanaka |
| 5,363,008 | A | 11/1994 | Hiramoto |
| 5,388,580 | A | 2/1995 | Sullivan |
| 5,402,462 | A | 3/1995 | Nobuta |
| 5,423,328 | A | 6/1995 | Gavish |
| 5,440,133 | A | 8/1995 | Moyers |
| 5,483,129 | A | 1/1996 | Yamamoto |
| 5,511,549 | A | 4/1996 | Legg |
| 5,538,494 | A * | 7/1996 | Matsuda ............ 600/1 |
| 5,568,109 | A | 10/1996 | Takayama |
| 5,576,549 | A | 11/1996 | Hell |
| 5,576,602 | A | 11/1996 | Hiramoto |
| 5,585,642 | A | 12/1996 | Britton |
| 5,600,213 | A | 2/1997 | Hiramoto |
| 5,626,682 | A | 5/1997 | Kobari |
| 5,633,907 | A | 5/1997 | Gravelle |
| 5,642,302 | A | 6/1997 | Dumont |
| 5,659,223 | A | 8/1997 | Goodman |
| 5,661,366 | A | 8/1997 | Hirota |
| 5,668,371 | A | 9/1997 | Deasy |
| 5,698,954 | A | 12/1997 | Hirota |
| 5,760,395 | A | 6/1998 | Johnstone |
| 5,789,875 | A | 8/1998 | Hiramoto |
| 5,790,997 | A | 8/1998 | Ruehl |
| 5,818,058 | A | 10/1998 | Nakanishi |
| 5,820,320 | A | 10/1998 | Kobari |
| 5,825,845 | A | 10/1998 | Blair |
| 5,825,847 | A | 10/1998 | Ruth |
| 5,866,912 | A | 2/1999 | Slater |
| 5,895,926 | A | 4/1999 | Britton |
| 5,907,595 | A | 5/1999 | Sommerer |
| 5,917,293 | A | 6/1999 | Saito |
| 5,969,367 | A | 10/1999 | Hiramoto |
| 5,986,274 | A | 11/1999 | Akiyama |
| 5,993,373 | A | 11/1999 | Nonaka |
| 6,008,499 | A | 12/1999 | Hiramoto |
| 6,034,377 | A | 3/2000 | Pu |
| 6,057,655 | A | 5/2000 | Jongen |
| 6,087,670 | A | 7/2000 | Hiramoto |
| 6,087,672 | A | 7/2000 | Matsuda |
| 6,148,058 | A | 11/2000 | Dobbs |
| 6,207,952 | B1 | 3/2001 | Kan |
| 6,218,675 | B1 | 4/2001 | Akiyama |
| 6,236,043 | B1 | 5/2001 | Tadokoro |
| 6,265,837 | B1 | 7/2001 | Akiyama |
| 6,282,263 | B1 | 8/2001 | Arndt |
| 6,316,776 | B1 | 11/2001 | Hiramoto |
| 6,322,249 | B1 | 11/2001 | Wofford |
| 6,335,535 | B1 | 1/2002 | Miyake |
| 6,339,635 | B1 | 1/2002 | Schardt |
| 6,356,617 | B1 | 3/2002 | Besch |
| 6,365,894 | B2 | 4/2002 | Tadokoro |
| 6,421,416 | B1 | 7/2002 | Sliski |
| 6,433,336 | B1 | 8/2002 | Jongen |
| 6,433,349 | B2 | 8/2002 | Akiyama |
| 6,433,494 | B1 | 8/2002 | Kulish |
| 6,437,513 | B1 | 8/2002 | Stelzer |
| 6,444,990 | B1 | 9/2002 | Morgan |
| 6,462,490 | B1 | 10/2002 | Matsuda |
| 6,470,068 | B2 | 10/2002 | Cheng |
| 6,472,834 | B2 | 10/2002 | Hiramoto |
| 6,476,403 | B1 | 11/2002 | Dolinskii |
| 6,545,436 | B1 | 4/2003 | Gary |
| 6,560,354 | B1 | 5/2003 | Maurer, Jr. |
| 6,580,084 | B1 | 6/2003 | Hiramoto |
| 6,597,005 | B1 | 7/2003 | Badura |
| 6,600,164 | B1 | 7/2003 | Badura |
| 6,614,038 | B1 | 9/2003 | Brand |
| 6,617,598 | B1 | 9/2003 | Matsuda |
| 6,626,842 | B2 | 9/2003 | Oka |
| 6,635,882 | B1 | 10/2003 | Pavlovic |
| 6,639,234 | B1 | 10/2003 | Badura |
| 6,670,618 | B1 | 12/2003 | Hartmann |
| 6,683,318 | B1 | 1/2004 | Haberer |
| 6,683,426 | B1 | 1/2004 | Kleeven |
| 6,710,362 | B2 | 3/2004 | Kraft |
| 6,717,162 | B1 | 4/2004 | Jongen |
| 6,725,078 | B2 | 4/2004 | Bucholz |
| 6,730,921 | B2 | 5/2004 | Kraft |
| 6,736,831 | B1 | 5/2004 | Hartmann |
| 6,745,072 | B1 | 6/2004 | Badura |
| 6,774,383 | B2 | 8/2004 | Norimine |
| 6,777,700 | B2 | 8/2004 | Yanagisawa |
| 6,785,359 | B2 | 8/2004 | Lemaitre |
| 6,787,771 | B2 | 9/2004 | Bashkirov |
| 6,792,078 | B2 | 9/2004 | Kato |
| 6,799,068 | B1 | 9/2004 | Hartmann |
| 6,800,866 | B2 | 10/2004 | Amemiya |
| 6,803,591 | B2 | 10/2004 | Muramatsu |
| 6,809,325 | B2 | 10/2004 | Dahl |
| 6,819,743 | B2 | 11/2004 | Kato |
| 6,822,244 | B2 | 11/2004 | Beloussov |
| 6,823,045 | B2 | 11/2004 | Kato |
| 6,838,676 | B1 | 1/2005 | Jackson |
| 6,842,502 | B2 | 1/2005 | Jaffray |
| 6,859,741 | B2 | 2/2005 | Haberer |

| | | |
|---|---|---|
| 6,862,469 B2 | 3/2005 | Bucholz |
| 6,873,123 B2 | 3/2005 | Marchand |
| 6,881,970 B2 | 4/2005 | Akiyama |
| 6,891,177 B1 | 5/2005 | Kraft |
| 6,897,451 B2 | 5/2005 | Kaercher |
| 6,900,446 B2 | 5/2005 | Akiyama |
| 6,903,351 B1 | 6/2005 | Akiyama |
| 6,903,356 B2 | 6/2005 | Muramatsu |
| 6,931,100 B2 | 8/2005 | Kato |
| 6,936,832 B2 | 8/2005 | Norimine |
| 6,937,696 B1 * | 8/2005 | Mostafavi ............... 378/95 |
| 6,953,943 B2 | 10/2005 | Yanagisawa |
| 6,979,832 B2 | 12/2005 | Yanagisawa |
| 6,984,835 B2 | 1/2006 | Harada |
| 6,992,312 B2 | 1/2006 | Yanagisawa |
| 6,998,258 B1 | 2/2006 | Kesseler |
| 7,012,267 B2 | 3/2006 | Moriyama |
| 7,026,636 B2 | 4/2006 | Yanagisawa |
| 7,030,396 B2 | 4/2006 | Muramatsu |
| 7,045,781 B2 | 5/2006 | Adamec |
| 7,049,613 B2 | 5/2006 | Yanagisawa |
| 7,053,389 B2 | 5/2006 | Yanagisawa |
| 7,054,801 B2 | 5/2006 | Sakamoto |
| 7,058,158 B2 | 6/2006 | Sako |
| 7,060,997 B2 | 6/2006 | Norimine |
| 7,071,479 B2 | 7/2006 | Yanagisawa |
| 7,081,619 B2 | 7/2006 | Bashkirov |
| 7,084,410 B2 | 8/2006 | Beloussov |
| 7,091,478 B2 | 8/2006 | Haberer |
| 7,102,144 B2 | 9/2006 | Matsuda |
| 7,109,505 B1 | 9/2006 | Sliski |
| 7,122,811 B2 | 10/2006 | Matsuda |
| 7,141,810 B2 | 11/2006 | Kakiuchi |
| 7,154,107 B2 | 12/2006 | Yanagisawa |
| 7,154,108 B2 | 12/2006 | Tadokoro |
| 7,173,264 B2 | 2/2007 | Moriyama |
| 7,173,265 B2 | 2/2007 | Miller |
| 7,193,227 B2 | 3/2007 | Hiramoto |
| 7,199,382 B2 | 4/2007 | Rigney |
| 7,208,748 B2 | 4/2007 | Sliski |
| 7,212,608 B2 | 5/2007 | Nagamine |
| 7,212,609 B2 | 5/2007 | Nagamine |
| 7,227,161 B2 | 6/2007 | Matsuda |
| 7,247,869 B2 | 7/2007 | Tadokoro |
| 7,252,745 B2 | 8/2007 | Gorokhovsky |
| 7,259,529 B2 | 8/2007 | Tanaka |
| 7,262,424 B2 | 8/2007 | Moriyama |
| 7,274,018 B2 | 9/2007 | Adamec |
| 7,274,025 B2 | 9/2007 | Berdermann |
| 7,280,633 B2 | 10/2007 | Cheng |
| 7,297,967 B2 | 11/2007 | Yanagisawa |
| 7,301,162 B2 | 11/2007 | Matsuda |
| 7,307,264 B2 | 12/2007 | Brusasco |
| 7,310,404 B2 | 12/2007 | Tashiro |
| 7,315,606 B2 | 1/2008 | Tsujii |
| 7,319,231 B2 | 1/2008 | Moriyama |
| 7,345,291 B2 | 3/2008 | Kats |
| 7,345,292 B2 | 3/2008 | Moriyama |
| 7,351,988 B2 | 4/2008 | Naumann |
| 7,355,189 B2 | 4/2008 | Yanagisawa |
| 7,356,112 B2 | 4/2008 | Brown |
| 7,368,740 B2 | 5/2008 | Beloussov |
| 7,372,053 B2 | 5/2008 | Yamashita |
| 7,381,979 B2 | 6/2008 | Yamashita |
| 7,385,203 B2 | 6/2008 | Nakayama |
| 7,394,082 B2 | 7/2008 | Fujimaki |
| 7,397,054 B2 | 7/2008 | Natori |
| 7,397,901 B1 | 7/2008 | Johnsen |
| 7,402,822 B2 | 7/2008 | Guertin |
| 7,402,823 B2 | 7/2008 | Guertin |
| 7,402,824 B2 | 7/2008 | Guertin |
| 7,402,963 B2 | 7/2008 | Sliski |
| 7,425,717 B2 | 9/2008 | Matsuda |
| 7,432,516 B2 | 10/2008 | Peggs |
| 7,439,528 B2 | 10/2008 | Nishiuchi |
| 7,446,490 B2 | 11/2008 | Jongen |
| 7,449,701 B2 | 11/2008 | Fujimaki |
| 7,456,415 B2 | 11/2008 | Yanagisawa |
| 7,456,591 B2 | 11/2008 | Jongen |
| 7,465,944 B2 | 12/2008 | Ueno |
| 7,471,765 B2 | 12/2008 | Jaffray |
| 7,476,883 B2 | 1/2009 | Nutt |
| 7,492,858 B2 | 2/2009 | Partain |
| 7,531,818 B2 | 5/2009 | Brahme |
| 7,555,103 B2 | 6/2009 | Johnsen |
| 7,560,717 B2 | 7/2009 | Matsuda |
| 7,576,342 B2 | 8/2009 | Hiramoto |
| 7,586,112 B2 | 9/2009 | Chiba |
| 7,589,334 B2 | 9/2009 | Hiramoto |
| 7,626,347 B2 | 12/2009 | Sliski |
| 7,634,057 B2 | 12/2009 | Ein-Gal |
| 7,659,521 B2 | 2/2010 | Pedroni |
| 7,668,585 B2 | 2/2010 | Green |
| 7,692,168 B2 | 4/2010 | Moriyama |
| 7,701,677 B2 | 4/2010 | Schultz |
| 7,709,818 B2 | 5/2010 | Matsuda |
| 7,718,982 B2 | 5/2010 | Sliski |
| 7,728,311 B2 | 6/2010 | Gall |
| 7,729,469 B2 * | 6/2010 | Kobayashi ............... 378/10 |
| 7,741,623 B2 | 6/2010 | Sommer |
| 7,755,305 B2 | 7/2010 | Umezawa |
| 7,772,577 B2 | 8/2010 | Saito |
| 7,796,730 B2 | 9/2010 | Marash |
| 7,801,277 B2 | 9/2010 | Zou |
| 7,807,982 B2 | 10/2010 | Nishiuchi |
| 7,817,774 B2 | 10/2010 | Partain |
| 7,817,778 B2 | 10/2010 | Nord |
| 7,825,388 B2 | 11/2010 | Nihongi |
| 7,826,592 B2 | 11/2010 | Jaffray |
| 7,826,593 B2 | 11/2010 | Svensson |
| 7,834,336 B2 | 11/2010 | Boeh |
| 7,838,855 B2 | 11/2010 | Fujii |
| 7,848,488 B2 | 12/2010 | Mansfield |
| 7,860,216 B2 | 12/2010 | Jongen |
| 7,875,868 B2 | 1/2011 | Moriyama |
| 7,894,574 B1 | 2/2011 | Nord |
| 7,906,769 B2 | 3/2011 | Blasche |
| 7,919,765 B2 | 4/2011 | Timmer |
| 7,939,809 B2 | 5/2011 | Balakin |
| 7,940,891 B2 | 5/2011 | Star-Lack |
| 7,940,894 B2 | 5/2011 | Balakin |
| 7,953,205 B2 * | 5/2011 | Balakin .................. 378/69 |
| 7,961,844 B2 | 6/2011 | Takeda |
| 7,977,656 B2 | 7/2011 | Fujimaki |
| 7,982,198 B2 | 7/2011 | Nishiuchi |
| 7,987,053 B2 | 7/2011 | Schaffner |
| 7,995,813 B2 | 8/2011 | Foshee |
| 8,003,964 B2 | 8/2011 | Stark |
| 8,009,804 B2 | 8/2011 | Siljamaki |
| 8,053,745 B2 * | 11/2011 | Moore ................. 250/492.1 |
| 2003/0015666 A1 * | 1/2003 | Morgan et al. ............. 250/398 |
| 2003/0163015 A1 | 8/2003 | Yanagisawa |
| 2003/0164459 A1 | 9/2003 | Schardt |
| 2004/0022361 A1 | 2/2004 | Lemaitre |
| 2004/0062354 A1 | 4/2004 | Kato |
| 2004/0155206 A1 | 8/2004 | Marchand |
| 2004/0218725 A1 | 11/2004 | Radley |
| 2004/0254492 A1 | 12/2004 | Zhang |
| 2005/0017193 A1 | 1/2005 | Jackson |
| 2005/0148808 A1 | 7/2005 | Cameron |
| 2005/0161618 A1 | 7/2005 | Pedroni |
| 2005/0211905 A1 | 9/2005 | Stark |
| 2005/0238134 A1 | 10/2005 | Brusasco |
| 2005/0269497 A1 | 12/2005 | Jongen |
| 2006/0050848 A1 | 3/2006 | Vilsmeier |
| 2006/0106301 A1 | 5/2006 | Kats |
| 2006/0171508 A1 | 8/2006 | Noda |
| 2006/0226372 A1 | 10/2006 | Yanagisawa |
| 2006/0255285 A1 | 11/2006 | Jongen |
| 2007/0018121 A1 | 1/2007 | Leyman |
| 2007/0040115 A1 | 2/2007 | Publicover |
| 2007/0093723 A1 | 4/2007 | Keall |
| 2007/0121788 A1 | 5/2007 | Mildner |
| 2007/0170994 A1 | 7/2007 | Peggs |
| 2007/0181815 A1 | 8/2007 | Ebstein |
| 2007/0228304 A1 | 10/2007 | Nishiuchi |
| 2008/0023644 A1 | 1/2008 | Pedroni |
| 2008/0093567 A1 | 4/2008 | Gall |

| | | |
|---|---|---|
| 2008/0139955 A1 | 6/2008 | Hansmann |
| 2008/0191142 A1 | 8/2008 | Pedroni |
| 2008/0267352 A1 | 10/2008 | Aoi |
| 2009/0096179 A1 | 4/2009 | Stark |
| 2009/0140672 A1 | 6/2009 | Gall |
| 2009/0168960 A1 | 7/2009 | Jongen |
| 2009/0184263 A1 | 7/2009 | Moriyama |
| 2009/0189095 A1 | 7/2009 | Flynn |
| 2009/0200483 A1 | 8/2009 | Gall |
| 2009/0236545 A1 | 9/2009 | Timmer |
| 2009/0283704 A1 | 11/2009 | Nishiuchi |
| 2009/0289194 A1 | 11/2009 | Saito |
| 2009/0304153 A1 | 12/2009 | Amelia |
| 2009/0309046 A1* | 12/2009 | Balakin ............... 250/492.3 |
| 2010/0001212 A1 | 1/2010 | Nishiuchi |
| 2010/0008468 A1 | 1/2010 | Balakin |
| 2010/0008469 A1 | 1/2010 | Balakin |
| 2010/0033115 A1 | 2/2010 | Cleland |
| 2010/0045213 A1 | 2/2010 | Sliski |
| 2010/0059688 A1 | 3/2010 | Claereboudt |
| 2010/0060209 A1 | 3/2010 | Balakin |
| 2010/0128846 A1 | 5/2010 | Balakin |
| 2010/0230617 A1 | 9/2010 | Gall |
| 2010/0272241 A1 | 10/2010 | Amelia |
| 2010/0308235 A1 | 12/2010 | Sliski |
| 2011/0073778 A1 | 3/2011 | Natori |
| 2011/0089329 A1 | 4/2011 | Jongen |
| 2011/0127443 A1 | 6/2011 | Comer |
| 2011/0137159 A1 | 6/2011 | Jongen |
| 2011/0147608 A1* | 6/2011 | Balakin ............... 250/396 R |
| 2011/0186720 A1 | 8/2011 | Jongen |
| 2011/0233423 A1 | 9/2011 | Balakin |

FOREIGN PATENT DOCUMENTS

WO    WO 2008/044194 A2    4/2008

OTHER PUBLICATIONS

Amaldi, "A Hospital-Based Hadrontherapy Complex", Journal, Jun. 27, 1994, pp. 49-51, XP002552288, Proceedings of Epac 94, London, England.

Arimoto, "A Study of the PRISM-FFAG Magnet", Journal, Oct. 18, 2004,Oct. 22, 2004, pp. 243-245, XP002551810, Proceedings of Cyclotron 2004 Conference, Tokyo, Japan.

Biophysics Group, "Design Construction and First Experiments of a Magnetic Scanning System for Therapy. Radiobiological Experiment on the Radiobiological Action of Carbon, Oxygen and Neon", Book, Jun. 1, 1991, pp. 1-31, XP009121701, vol. GSI-91-18, GSI Report, Darmstadt ,DE.

Blackmore, "Operation of the TRIUMF Proton Therapy Facility", Book, May 12, 1997, pp. 3831-3833, XP010322373, vol. 3, Proceedings of the 1997 Particle Accelerator Conference, NJ, USA.

Bryant, "Proton-Ion Medical Machine Study (PIMMS) Part II", Book, Jul. 27, 2000, p. 23,p. 228,pp. 289-290, XP002551811, European Organisation for Nuclear Research Cern-Ps Division, Geneva, Switzerland.

Craddock, "New Concepts in FFAG Design for Secondary Beam Facilities and other Applications", Journal, May 16, 2005,May 20, 2005, pp. 261-265, XP002551806, Proceedings of 2005 Particle Accelerator Conference, Knoxville, Tennessee, USA.

Dzhelepov, "Use of USSR Proton Accelerators for Medical Purposes", Journal,Jun. 1973, pp. 268-270, vol. ns-2- No. 3, XP002553045, IEEE Transactions on Nuclear Science USA, USA.

Endo, "Medical Synchrotron for Proton Therapy" Journal, Jun. 7, 1988,Jun. 11, 1988, pp. 1459-1461, XP002551808, Proceedings of Epac 88, Rome, Italy.

Johnstone, Koscielniak, "Tune-Stabilized Linear-Field FFAG for Carbon Therapy", Journal, Jun. 26, 2006,Jun. 30, 2006, XP002551807, Proceedings of Epac 2006, Edinburgh, Scotland, UK.

Kalnins, "The use of electric multipole lenses for bending and focusing polar molecules, with application to the design of a rotational-state separator", Journal, May 17, 2003,May 21, 2003, pp. 2951-2953, XP002554356, Proceeding of Pac 2003, Portland, Oregon, USA.

Kim, "50 MeV Proton Beam Test Facility for Low Flux Beam Utilization Studies of PEFP", Journal, Oct. 31, 2005, pp. 441-443, XP002568008, Proceedings of Apac 2004, Pohang, Korea.

Lapostolle, "Introduction a la theorie des accelerateurs lineaires", Book, Jul. 10, 1987, pp. 4-5, XP002554354, Cern Yellow Book Cern, Geneva, Switzerland.

Li, "A thin Beryllium Injection Window for CESR-C", Book, May 12, 2003, pp. 2264-2266, XP002568010, vol. 4, PAC03, Portland, Oregon, USA.

Noda, "Slow beam extraction by a transverse RF field with AM and FM", Journal, May 21, 1996, pp. 269-277, vol. A374, XP002552289, Nuclear Instruments and Methods in Physics Research A, Eslevier, Amsterdam, NL.

Noda, "Performance of a respiration-gated beam control system for patient treatment", Journal, Jun. 10, 1996,Jun. 14, 1996, pp. 2656-2658, XP002552290, Proceedings Epac 96, Barcelona, Spain.

Peters, "Negative ion sources for high energy accelerators", Journal, Feb. 1, 2000, pp. 1069-1074, XP012037926, vol. 71-No. 2,Review of Scientific Instruments, Melville, NY, USA.

Pohlit, "Optimization of Cancer Treatment with Accelerator Produced Radiations", Journal, Jun. 22, 1998, pp. 192-194, XP002552855, Proceedings Epac 98, Stockholm, Sweden.

Saito, "RF Accelerating System for Compact Ion Synchrotron", Journal, Jun. 18, 2001, pp. 966-968, XP002568009, Proceeding of 2001 Pac, Chicago, USA.

Suda, "Medical Application of the Positron Emitter Beam at HIMAC", Journal, Jun. 26, 2000, Jun. 30, 2000, pp. 2554-2556, XP002553046, Proceedings of Epac 2000, Vienna, Austria.

Tanigaki, "Construction of FFAG Accelerators in KURRI for ADS Study", May 16, 2005,May 20, 2005, pp. 350-352, XP002551809, Proceedings of 2005 Particle Accelerator Conference, Knoxville, Tennessee, USA.

Trbojevic, "Design of a Non-Scaling FFAG Accelerator for Proton Therapy", Journal, Oct. 18, 2004,Oct. 22, 2004, pp. 246-248, XP002551805, Proceedings of 2004 Cyclotron Conference, Tokyo, Japan.

Winkler, "Charge Exchange Extraction at the Experimental Storage Ring ESR at GSI", Journal, Jun. 22, 1998, p. 559-561, XP002552287, Proceedings of Epac 98, Stockholm, Sweden.

European Organization for Nuclear Research Cern, Jul. 27, 2000, pp. 1-352.

Proceeding of 2004 Cycloron Conference, Oct. 18, 2004.

Proceeding of 2004 Cyclotron Conference, Oct. 18, 2004, pp. 246-428.

Proceedings of EPAC 2006, Jun. 30, 2006, pp. 2290-2292.

Proceeding of 2005 Particle Accelerator Conference, May 16, 2005, pp. 261-265.

* cited by examiner

CHARGED PARTICLE CANCER THERAPY AND PATIENT BREATH MONITORING METHOD AND APPARATUS

CROSS REFERENCES TO RELATED APPLICATIONS

This application:
is a continuation-in-part of U.S. patent application Ser. No. 12/425,683 filed Apr. 17, 2009, now U.S. Pat. No. 7,939,809 which claims the benefit of:
U.S. provisional patent application No. 61/055,395 filed May 22, 2008;
U.S. provisional patent application No. 61/137,574 filed Aug. 1, 2008;
U.S. provisional patent application No. 61/192,245 filed Sep. 17, 2008;
U.S. provisional patent application No. 61/055,409 filed May 22, 2008;
U.S. provisional patent application No. 61/203,308 filed Dec. 22, 2008;
U.S. provisional patent application No. 61/188,407 filed Aug. 11, 2008;
U.S. provisional patent application No. 61/188,406 filed Aug. 11, 2008;
U.S. provisional patent application No. 61/189,815 filed Aug. 25, 2008;
U.S. provisional patent application No. 61/201,731 filed Dec. 15, 2008;
U.S. provisional patent application No. 61/205,362 filed Jan. 21, 2009;
U.S. provisional patent application No. 61/134,717 filed Jul. 14, 2008;
U.S. provisional patent application No. 61/134,707 filed Jul. 14, 2008;
U.S. provisional patent application No. 61/201,732 filed Dec. 15, 2008;
U.S. provisional patent application No. 61/198,509 filed Nov. 7, 2008;
U.S. provisional patent application No. 61/134,718 filed Jul. 14, 2008;
U.S. provisional patent application No. 61/190,613 filed Sep. 2, 2008;
U.S. provisional patent application No. 61/191,043 filed Sep. 8, 2008;
U.S. provisional patent application No. 61/192,237 filed Sep. 17, 2008;
U.S. provisional patent application No. 61/201,728 filed Dec. 15, 2008;
U.S. provisional patent application No. 61/190,546 filed Sep. 2, 2008;
U.S. provisional patent application No. 61/189,017 filed Aug. 15, 2008;
U.S. provisional patent application No. 61/198,248 filed Nov. 5, 2008;
U.S. provisional patent application No. 61/198,508 filed Nov. 7, 2008;
U.S. provisional patent application No. 61/197,971 filed Nov. 3, 2008;
U.S. provisional patent application No. 61/199,405 filed Nov. 17, 2008;
U.S. provisional patent application No. 61/199,403 filed Nov. 17, 2008; and
U.S. provisional patent application No. 61/199,404 filed Nov. 17, 2008;
claims the benefit of U.S. provisional patent application No. 61/209,529 filed Mar. 9, 2009;
claims the benefit of U.S. provisional patent application No. 61/208,182 filed Feb. 23, 2009; and
claims the benefit of U.S. provisional patent application No. 61/208,971 filed Mar. 3, 2009;
all of which are incorporated herein in their entirety by this reference thereto.

BACKGROUND OF THE INVENTION

1. Field of the Invention

This invention relates generally to treatment of solid cancers. More particularly, the invention relates to patient respiration monitoring and/or control elements used in conjunction with charged particle cancer therapy beam acceleration, extraction, and/or targeting methods and apparatus.

2. Discussion of the Prior Art

Cancer

A tumor is an abnormal mass of tissue. Tumors are either benign or malignant. A benign tumor grows locally, but does not spread to other parts of the body. Benign tumors cause problems because of their spread, as they press and displace normal tissues. Benign tumors are dangerous in confined places such as the skull. A malignant tumor is capable of invading other regions of the body. Metastasis is cancer spreading by invading normal tissue and spreading to distant tissues.

Cancer Treatment

Several forms of radiation therapy exist for cancer treatment including: brachytherapy, traditional electromagnetic X-ray therapy, and proton therapy. Each are further described, infra.

Brachytherapy is radiation therapy using radioactive sources implanted inside the body. In this treatment, an oncologist implants radioactive material directly into the tumor or very close to it. Radioactive sources are also placed within body cavities, such as the uterine cervix.

The second form of traditional cancer treatment using electromagnetic radiation includes treatment using X-rays and gamma rays. An X-ray is high-energy, ionizing, electromagnetic radiation that is used at low doses to diagnose disease or at high doses to treat cancer. An X-ray or Röntgen ray is a form of electromagnetic radiation with a wavelength in the range of 10 to 0.01 nanometers (nm), corresponding to frequencies in the range of 30 PHz to 30 EHz. X-rays are longer than gamma rays and shorter than ultraviolet rays. X-rays are primarily used for diagnostic radiography. X-rays are a form of ionizing radiation and as such can be dangerous. Gamma rays are also a form of electromagnetic radiation and are at frequencies produced by sub-atomic particle interactions, such as electron-positron annihilation or radioactive decay. In the electromagnetic spectrum, gamma rays are generally characterized as electromagnetic radiation having the highest frequency, as having highest energy, and having the shortest wavelength, such as below about 10 picometers. Gamma rays consist of high energy photons with energies above about 100 keV. X-rays are commonly used to treat cancerous tumors. However, X-rays are not optimal for treatment of cancerous tissue as X-rays deposit their highest does of radiation near the surface of the targeted tissue and delivery exponentially less radiation as they penetrate into the tissue. This results in large amounts of radiation being delivered outside of the tumor. Gamma rays have similar limitations.

The third form of cancer treatment uses protons. Proton therapy systems typically include: a beam generator, an accelerator, and a beam transport system to move the resulting accelerated protons to a plurality of treatment rooms where the protons are delivered to a tumor in a patient's body.

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Due to their relatively enormous size, protons scatter less easily in the tissue and there is very little lateral dispersion. Hence, the proton beam stays focused on the tumor shape without much lateral damage to surrounding tissue. All protons of a given energy have a certain range, defined by the Bragg peak, and the dosage delivery to tissue ratio is maximum over just the last few millimeters of the particle's range. The penetration depth depends on the energy of the particles, which is directly related to the speed to which the particles were accelerated by the proton accelerator. The speed of the proton is adjustable to the maximum rating of the accelerator. It is therefore possible to focus the cell damage due to the proton beam at the very depth in the tissues where the tumor is situated. Tissues situated before the Bragg peak receive some reduced dose and tissues situated after the peak receive none.

Synchrotron

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Extraction

T. Nakanishi, et. al. "Charged-Particle Beam Accelerator, Particle Beam Radiation Therapy System Using the Charged-Particle Beam Accelerator, and Method of Operating the Particle Beam Radiation Therapy System", U.S. Pat. No. 7,122,978 (Oct. 17, 2006) describe a charged particle beam accelerator having an RF-KO unit for increasing amplitude of betatron oscillation of a charged particle beam within a stable region of resonance and an extraction quadrupole electromagnet unit for varying a stable region of resonance. The RF-KO unit is operated within a frequency range in which the circulating beam does not go beyond a boundary of stable region of resonance and the extraction quadrupole electromagnet is operated with timing required for beam extraction.

T. Haberer, et. al. "Method and Device for Controlling a Beam Extraction Raster Scan Irradiation Device for Heavy Ions or Protons", U.S. Pat. No. 7,091,478 (Aug. 15, 2006) describe a method for controlling beam extraction irradiation in terms of beam energy, beam focusing, and beam intensity for every accelerator cycle.

K. Hiramoto, et. al. "Accelerator and Medical System and Operating Method of the Same", U.S. Pat. No. 6,472,834 (Oct. 29, 2002) describe a cyclic type accelerator having a deflection electromagnet and four-pole electromagnets for making a charged particle beam circulate, a multi-pole electromagnet for generating a stability limit of resonance of betatron oscillation, and a high frequency source for applying a high frequency electromagnetic field to the beam to move the beam to the outside of the stability limit. The high frequency source generates a sum signal of a plurality of alternating current (AC) signals of which the instantaneous frequencies change with respect to time, and of which the average values of the instantaneous frequencies with respect to time are different. The system applies the sum signal via electrodes to the beam.

K. Hiramoto, et. al. "Synchrotron Type Accelerator and Medical Treatment System Employing the Same", U.S. Pat. No. 6,087,670 (Jul. 11, 2000) and K. Hiramoto, et. al. "Synchrotron Type Accelerator and Medical Treatment System Employing the Same", U.S. Pat. No. 6,008,499 (Dec. 28, 1999) describe a synchrotron accelerator having a high frequency applying unit arranged on a circulating orbit for applying a high frequency electromagnetic field to a charged particle beam circulating and for increasing amplitude of betatron oscillation of the particle beam to a level above a stability limit of resonance. Additionally, for beam ejection, four-pole divergence electromagnets are arranged: (1) downstream with respect to a first deflector; (2) upstream with respect to a deflecting electromagnet; (3) downstream with respect to the deflecting electromagnet; and (4) and upstream with respect to a second deflector.

K. Hiramoto, et. al. "Circular Accelerator and Method and Apparatus for Extracting Charged-Particle Beam in Circular Accelerator", U.S. Pat. No. 5,363,008 (Nov. 8, 1994) describe a circular accelerator for extracting a charged-particle beam that is arranged to: (1) increase displacement of a beam by the effect of betatron oscillation resonance; (2) to increase the betatron oscillation amplitude of the particles, which have an initial betatron oscillation within a stability limit for resonance; and (3) to exceed the resonance stability limit thereby extracting the particles exceeding the stability limit of the resonance.

K. Hiramoto, et. al. "Method of Extracting Charged Particles from Accelerator, and Accelerator Capable Carrying Out the Method, by Shifting Particle Orbit", U.S. Pat. No. 5,285,166 (Feb. 8, 1994) describe a method of extracting a charged particle beam. An equilibrium orbit of charged particles maintained by a bending magnet and magnets having multipole components greater than sextuple components is shifted by a constituent element of the accelerator other than these magnets to change the tune of the charged particles.

Respiration

K. Matsuda "Radioactive Beam Irradiation Method and Apparatus Taking Movement of the Irradiation Area Into Consideration", U.S. Pat. No. 5,538,494 (Jul. 23, 1996) describes a method and apparatus that enables irradiation even in the case of a diseased part changing position due to physical activity, such as breathing and heart beat. Initially, a position change of a diseased body part and physical activity of the patient are measured concurrently and a relationship therebetween is defined as a function. Radiation therapy is performed in accordance to the function.

Patient Positioning

Y. Nagamine, et. al. "Patient Positioning Device and Patient Positioning Method", U.S. Pat. Nos. 7,212,609 and 7,212,608 (May 1, 2007) describe a patient positioning system that compares a comparison area of a reference X-ray image and a current X-ray image of a current patient location using pattern matching.

D. Miller, et. al. "Modular Patient Support System", U.S. Pat. No. 7,173,265 (Feb. 6, 2007) describe a radiation treatment system having a patient support system that includes a modularly expandable patient pod and at least one immobilization device, such as a moldable foam cradle.

K. Kato, et. al. "Multi-Leaf Collimator and Medical System Including Accelerator", U.S. Pat. No. 6,931,100 (Aug. 16, 2005); K. Kato, et. al. "Multi-Leaf Collimator and Medical System Including Accelerator", U.S. Pat. No. 6,823,045 (Nov. 23, 2004); K. Kato, et. al. "Multi-Leaf Collimator and Medical System Including Accelerator", U.S. Pat. No. 6,819,743 (Nov. 16, 2004); and K. Kato, et. al. "Multi-Leaf Collimator and Medical System Including Accelerator", U.S. Pat. No. 6,792,078 (Sep. 14, 2004) all describe a system of leaf plates used to shorten positioning time of a patient for irradiation therapy. Motor driving force is transmitted to a plurality of leaf plates at the same time through a pinion gear. The system also uses upper and lower air cylinders and upper and lower guides to position a patient.

Problem

There exists in the art of particle beam therapy of cancerous tumors a need for monitoring and verification of proper patient respiration or breath control immediately prior to and/or concurrently with particle beam therapy irradiation to ensure targeted and controlled delivery of energy to the cancerous tumor with minimization of damage to surrounding healthy tissue. There further exists in the art of particle beam treatment of cancerous tumors in the body a need for efficient control of magnetic fields used in the control of charged particles in a synchrotron of a charged particle cancer therapy system to deliver charged particles with a specified energy, intensity, and/or timing of charged particle delivery relative to a patient's respiration cycle. Still further, there exists a need for efficient, precise, and/or accurate noninvasive, in-vivo treatment of a solid cancerous tumor with minimization of damage to surrounding healthy tissue in a patient and with efficient usage of synchrotron time.

SUMMARY OF THE INVENTION

The invention comprises a patient respiration or breath monitoring and/or control method and apparatus used in conjunction with multi-axis controlled charged particle beam radiation therapy of cancerous tumors.

DETAILED DESCRIPTION OF THE INVENTION

Figure 1:
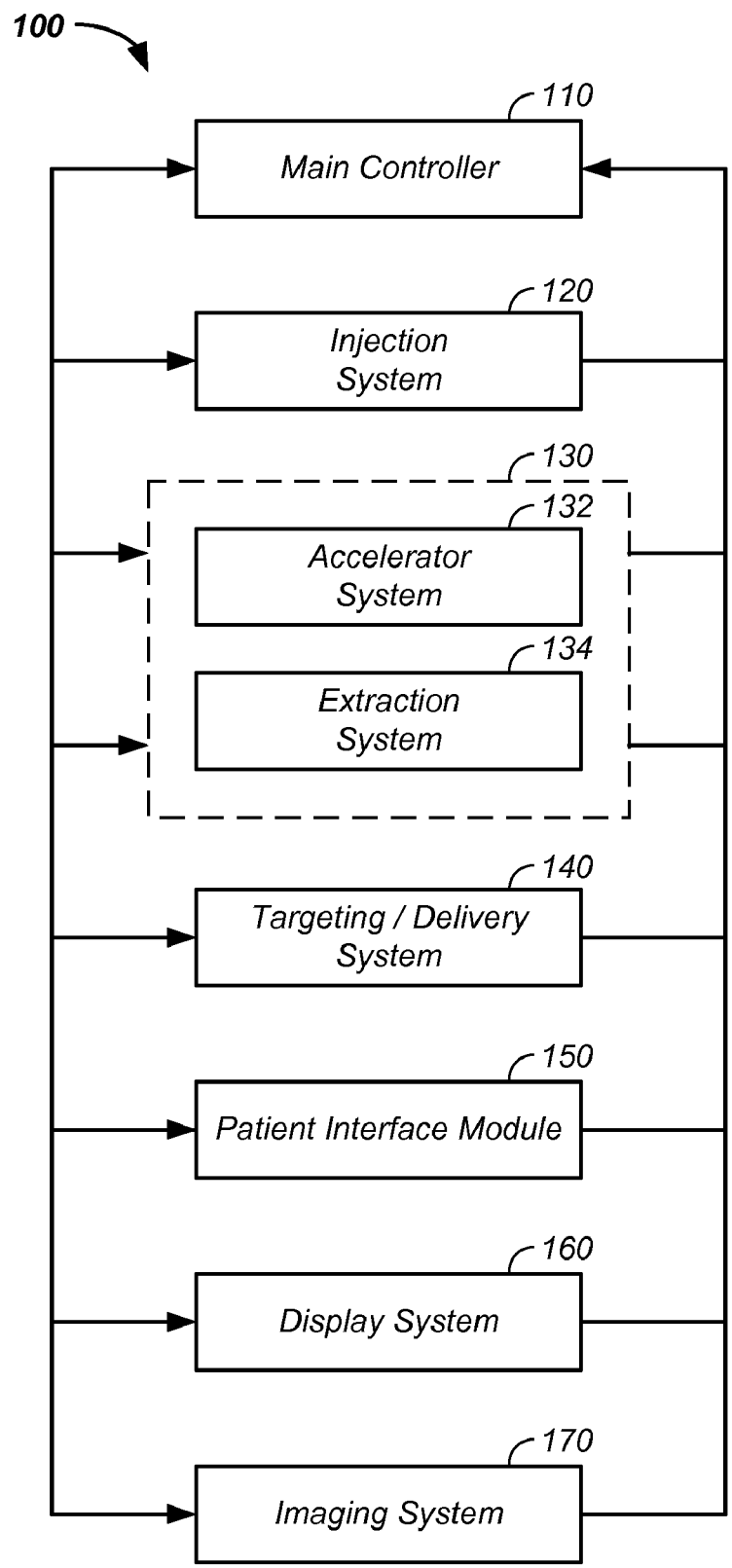
FIG. 1 illustrates component connections of a particle beam therapy system.

The invention comprises a patient respiration monitoring and/or control method and apparatus used in conjunction with charged particle beam radiation therapy of cancerous tumors.

Accurate and precise delivery of protons to a tumor in body tissue is critical in charged particle beam therapy. Complicating accurate and precise deliver is natural movement of the body. One form or movement of the body is related to respiration of the patient, which results in movements throughout the body and especially in the chest cavity of the patient. The movement results in relative movement of internal body parts, such as organs, as a function of time. Hence, a method of determining position of elements of the body at and/or in close proximity in time to the charged particle therapy is needed. Herein, patient respiration monitoring and/or control methods and apparatus used in conjunction with charged particle therapy are described. Particularly, a patient respiration or breath monitoring and/or control method and apparatus used in conjunction with multi-axis charged particle or proton beam radiation therapy of cancerous tumors is described. The respiration monitoring system uses thermal and/or force sensors to determine where a patient is in a breathing or respiration cycle in combination with a feedback signal control delivered to the patient to inform the patient when breath control is required. The resulting respiration control is timed with charged particle delivery to the tumor to enhance accuracy, precision, and efficiency of tumor treatment.

Used in conjunction with the respiration monitoring system, novel features of a synchrotron are described. Particularly, intensity control of a charged particle beam acceleration, extraction, and/or targeting method and apparatus used in conjunction with charged particle beam radiation therapy of cancerous tumors is described. More particularly, intensity control of a charged particle stream of a synchrotron is described. Intensity control is described in combination with turning magnets, edge focusing magnets, concentrating magnetic field magnets, winding and control coils, and extraction elements of the synchrotron. The synchrotron control elements allow tight control of the charged particle beam, which compliments the tight control of patient positioning to yield efficient treatment of a solid tumor with reduced tissue damage to surrounding healthy tissue. In addition, the system reduces the overall size of the synchrotron, provides a tightly controlled proton beam, directly reduces the size of required magnetic fields, directly reduces required operating power, and allows continual acceleration of protons in a synchrotron even during a process of extracting protons from the synchrotron.

Cyclotron/Synchrotron

A cyclotron uses a constant magnetic field and a constant-frequency applied electric field. One of the two fields is varied in a synchrocyclotron. Both of these fields are varied in a synchrotron. Thus, a synchrotron is a particular type of cyclic particle accelerator in which a magnetic field is used to turn the particles so they circulate and an electric field is used to accelerate the particles. The synchroton carefully synchronizes the applied fields with the travelling particle beam.

By increasing the fields appropriately as the particles gain energy, the charged particles path can be held constant as they are accelerated. This allows the vacuum container for the particles to be a large thin torus. In practice it is easier to use some straight sections between the bending magnets and some turning sections giving the torus the shape of a round-cornered polygon. A path of large effective radius is thus constructed using simple straight and curved pipe segments, unlike the disc-shaped chamber of the cyclotron type devices. The shape also allows and requires the use of multiple magnets to bend the particle beam.

The maximum energy that a cyclic accelerator can impart is typically limited by the strength of the magnetic fields and the minimum radius/maximum curvature, of the particle path. In a cyclotron the maximum radius is quite limited as the particles start at the center and spiral outward, thus this entire path must be a self-supporting disc-shaped evacuated chamber. Since the radius is limited, the power of the machine becomes limited by the strength of the magnetic field. In the case of an ordinary electromagnet, the field strength is limited by the saturation of the core because when all magnetic domains are aligned the field may not be further increased to any practical extent. The arrangement of the single pair of magnets also limits the economic size of the device.

Synchrotrons overcome these limitations, using a narrow beam pipe surrounded by much smaller and more tightly focusing magnets. The ability of this device to accelerate particles is limited by the fact that the particles must be charged to be accelerated at all, but charged particles under acceleration emit photons, thereby losing energy. The limiting beam energy is reached when the energy lost to the lateral acceleration required to maintain the beam path in a circle equals the energy added each cycle. More powerful accelerators are built by using large radius paths and by using more numerous and more powerful microwave cavities to accelerate the particle beam between corners. Lighter particles, such as electrons, lose a larger fraction of their energy when turning. Practically speaking, the energy of electron/positron accelerators is limited by this radiation loss, while it does not play a significant role in the dynamics of proton or ion accelerators. The energy of those is limited strictly by the strength of magnets and by the cost.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. Any charged particle beam system is equally applicable to the techniques described herein.

Referring now to FIG. 1, a charged particle beam system 100 is illustrated. The charged particle beam preferably comprises a number of subsystems including any of: a main controller 110; an injection system 120; a synchrotron 130 that typically includes: (1) an accelerator system 132 and (2) an extraction system 134; a targeting/delivery system 140; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 then optionally controls the injection system 120 to inject a proton into a synchrotron 130. The synchrotron typically contains at least an accelerator system 132 and an extraction system 134. The main controller preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the targeting/delivery system 140 to the patient interface module 150. One or more components of the patient interface module 150 are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Synchrotron

Herein, the term synchrotron is used to refer to a system maintaining the charged particle beam in a circulating path; however, cyclotrons are alternatively used, albeit with their inherent limitations of energy, intensity, and extraction control. Further, the charged particle beam is referred to herein as circulating along a circulating path about a central point of the synchrotron. The circulating path is alternatively referred to as an orbiting path; however, the orbiting path does not refer a perfect circle or ellipse, rather it refers to cycling of the protons around a central point or region.

Figure 2:
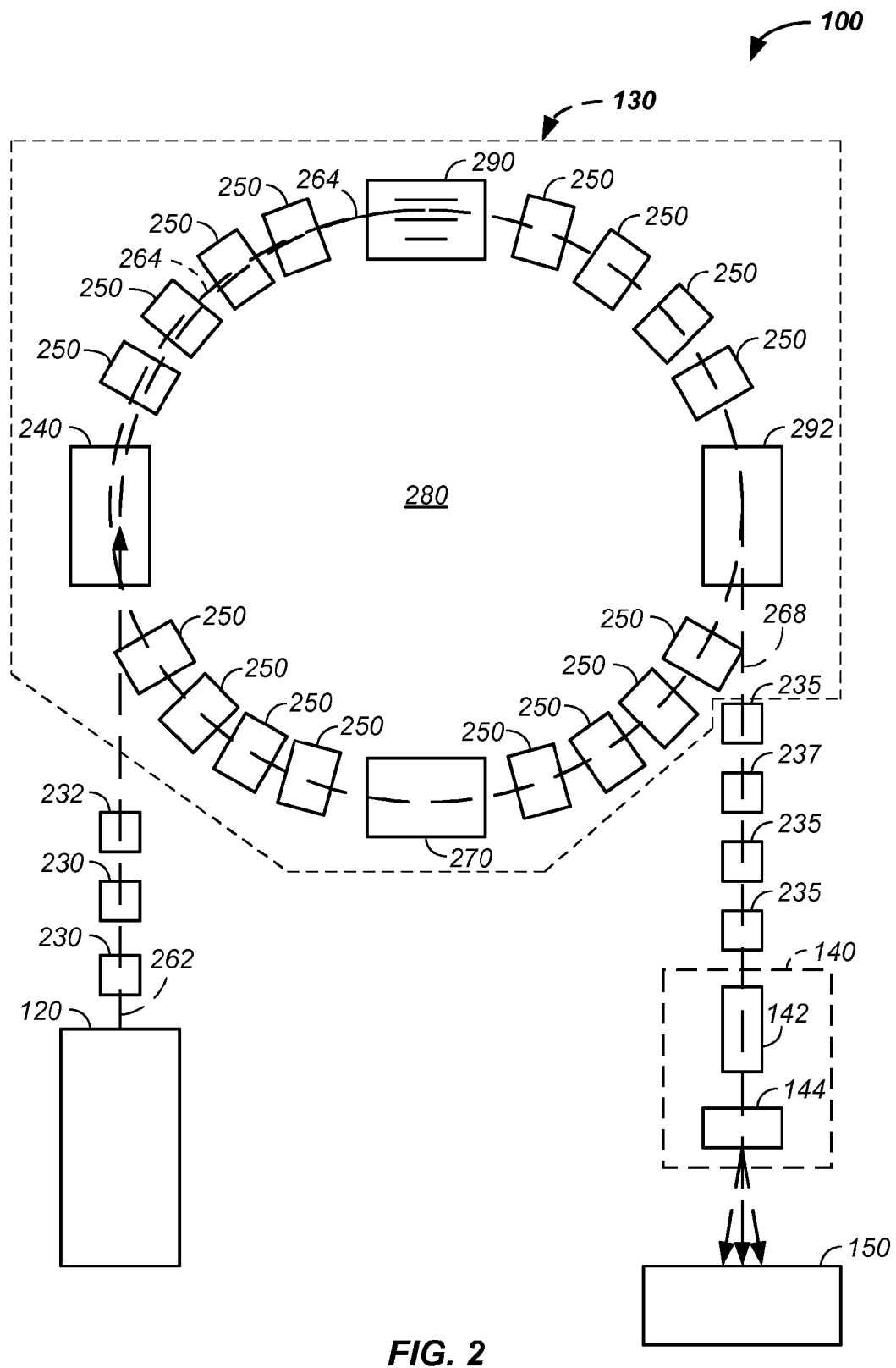
FIG. 2 illustrates a charged particle therapy system.

Referring now to FIG. 2, an illustrative exemplary embodiment of one version of the charged particle beam system 100 is provided. The number, position, and described type of components is illustrative and non-limiting in nature. In the illustrated embodiment, the injection system 120 or ion source or charged particle beam source generates protons. The protons are delivered into a vacuum tube that runs into, through, and out of the synchrotron. The generated protons are delivered along an initial path 262. Focusing magnets 230, such as quadrupole magnets or injection quadrupole magnets, are used to focus the proton beam path. A quadrupole magnet is a focusing magnet. An injector bending magnet 232 bends the proton beam toward the plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Main bending or turning magnets, dipole magnets, or circulating magnets 250 are used to turn the protons along a circulating beam path 264. A dipole magnet is a bending magnet. The main bending magnets 250 bend the initial beam path 262 into a circulating beam path 264. In this example, the main bending magnets 250 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets 250 are increased. Particularly, the speed of the protons achieved by the accelerator 270 are synchronized with magnetic fields of the main bending magnets 250 or circulating magnets to maintain stable circulation of the protons about a central point or region 280 of the synchrotron. At separate points in time the accelerator 270/main bending magnet 250 combination is used to accelerate and/or decelerate the circulating protons while maintaining the protons in the circulating path or orbit. An extraction element of the inflector/deflector system 290 is used in combination with a Lamberson extraction magnet 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a transport path 268 into the scanning/targeting/delivery system 140. Two components of a scanning system 140 or targeting system typically include a first axis control 142, such as a vertical control, and a second axis control 144, such as a horizontal control. In one embodiment, the first axis control 142 allows for about 100 mm of vertical or y-axis scanning of the proton beam 268 and the second axis control 144 allows for about 700 mm of horizontal or x-axis scanning of the proton beam 268. A nozzle system is optionally used for imaging the proton beam and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations. Use of the above listed elements is further described, infra. Protons are delivered with control to the patient interface module 170 and to a tumor of a patient.

In one example, the charged particle irradiation includes a synchrotron having: a center, straight sections, and turning sections. The charged particle beam path runs about the center, through the straight sections, and through the turning sections, where each of the turning sections comprises a plurality of bending magnets. Preferably, the circulation beam path comprises a length of less than sixty meters, and the number of straight sections equals the number of turning sections. Preferably no quadrupoles are used in or around the circulating path of the synchrotron.

Circulating System

A synchrotron 130 preferably comprises a combination of straight sections 310 and ion beam turning sections 320. Hence, the circulating path of the protons is not circular in a synchrotron, but is rather a polygon with rounded corners.

In one illustrative embodiment, the synchrotron 130, which is also referred to as an accelerator system, has four straight elements and four turning sections. Examples of straight sections 310 include the: inflector 240, accelerator 270, extraction system 290, and deflector 292. Along with the four straight sections are four ion beam turning sections 320, which are also referred to as magnet sections or turning sections. Turning sections are further described, infra.

Figure 3:
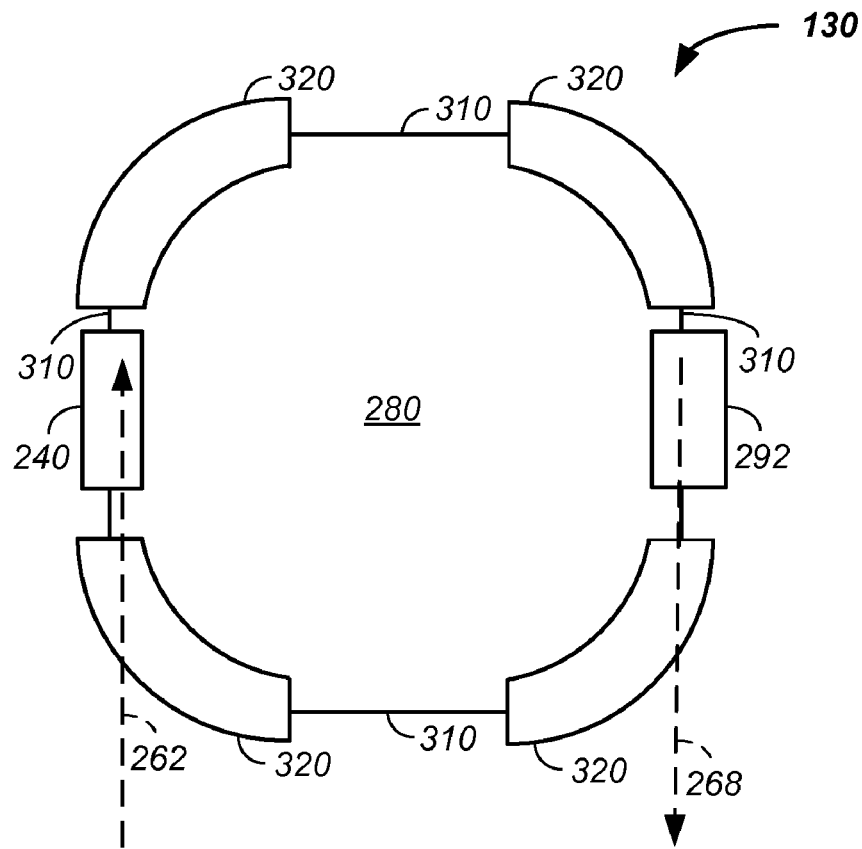
FIG. 3 illustrates straight and turning sections of a synchrotron

Referring now to FIG. 3, an exemplary synchrotron is illustrated. In this example, protons delivered along the initial path 262 are inflected into the circulating beam path with the inflector 240 and after acceleration are extracted via a deflector 292 to a beam transport path 268. In this example, the synchrotron 130 comprises four straight sections 310 and four turning sections 320 where each of the four turning sections use one or more magnets to turn the proton beam about ninety degrees. As is further described, infra, the ability to closely space the turning sections and efficiently turn the proton beam results in shorter straight sections. Shorter straight sections allows for a synchrotron design without the use of focusing quadrupoles in the circulating beam path of the synchrotron. The removal of the focusing quadrupoles from the circulating proton beam path results in a more compact design. In this example, the illustrated synchrotron has about a five meter diameter versus eight meter and larger cross-sectional diameters for systems using a quadrupole focusing magnet in the circulating proton beam path.

Figure 4:
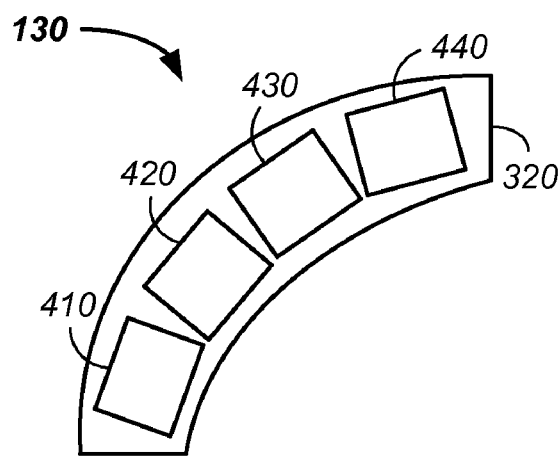
FIG. 4 illustrates turning magnets of a synchrotron.

Referring now to FIG. 4, additional description of the first turning section 320 is provided. Each of the turning sections preferably comprises multiple magnets, such as about 2, 4, 6, 8, 10, or 12 magnets. In this example, four turning magnets 410, 420, 430, 440 in the first turning section 320 are used to illustrate key principles, which are the same regardless of the number of magnets in a turning section 320. A turning magnet 410 is a particular type of circulating magnet 250.

In physics, the Lorentz force is the force on a point charge due to electromagnetic fields. The Lorentz force is given by the equation 1 in terms of magnetic fields with the election field terms not included.

$$F = q(v \times B) \qquad \text{eq. 1}$$

In equation 1, F is the force in newtons; B is the magnetic field in Teslas; and v is the instantaneous velocity of the particles in meters per second.

Figure 5:
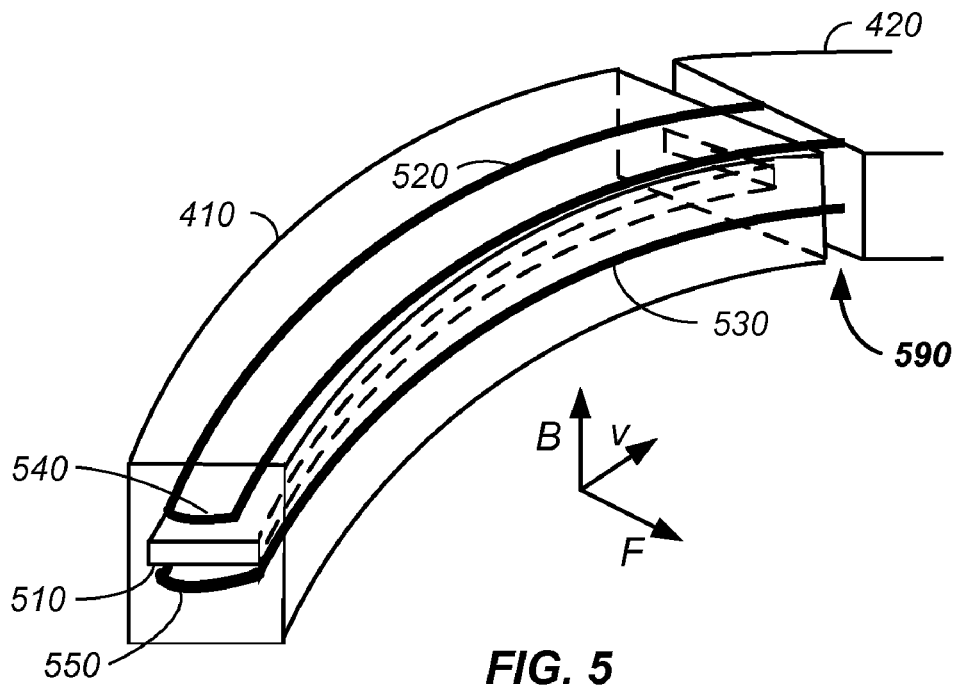
FIG. 5 provides a perspective view of a turning magnet.

Referring now to FIG. 5, an example of a single magnet turning section 410 is expanded. The turning section includes a gap 510. The gap is preferably a flat gap, allowing for a magnetic field across the gap that is more uniform, even, and intense. A magnetic field enters the gap through a magnetic field incident surface and exits the gap through a magnetic field exiting surface. The gap 510 runs in a vacuum tube between two magnet halves. The gap is controlled by at least two parameters: (1) the gap 510 is kept as large as possible to minimize loss of protons and (2) the gap 510 is kept as small as possible to minimize magnet sizes and the associated size and power requirements of the magnet power supplies. The flat nature of the gap 510 allows for a compressed and more uniform magnetic field across the gap. One example of a gap dimension is to accommodate a vertical proton beam size of about two centimeters with a horizontal beam size of about five to six centimeters.

As described, supra, a larger gap size requires a larger power supply. For instance, if the gap size doubles in vertical size, then the power supply requirements increase by about a factor of four. The flatness of the gap is also important. For example, the flat nature of the gap allows for an increase in energy of the extracted protons from about 250 to about 330 MeV. More particularly, if the gap 510 has an extremely flat surface, then the limits of a magnetic field of an iron magnet are reachable. An exemplary precision of the flat surface of the gap 510 is a polish of less than about five microns and preferably with a polish of about one to three micrometers. Unevenness in the surface results in imperfections in the applied magnetic field. The polished flat surface spreads unevenness of the applied magnetic field.

Still referring to FIG. 5, the charged particle beam moves through the gap with an instantaneous velocity, v. A first magnetic coil 520 and a second magnetic coil 530 run above and below the gap 510, respectively. Current running through the coils 520, 530 results in a magnetic field, B, running through the single magnet turning section 410. In this example, the magnetic field, B, runs upward, which results in a force, F, pushing the charged particle beam inward toward a central point of the synchrotron, which turns the charged particle beam in an arc.

Still referring to FIG. 5, a portion of an optional second magnet turning section 420 is illustrated. The coils 520, 530 typically have return elements 540, 550 or turns at the end of one magnet, such as at the end of the first magnet turning section 410. The return elements 540, 550 take space. The space reduces the percentage of the path about one orbit of the synchrotron that is covered by the turning magnets. This leads to portions of the circulating path where the protons are not turned and/or focused and allows for portions of the circulating path where the proton path defocuses. Thus, the space results in a larger synchrotron. Therefore, the space between magnet turning sections 560 is preferably minimized. The second turning magnet is used to illustrate that the coils 520, 530 optionally run along a plurality of magnets, such as 2, 3, 4, 5, 6, or more magnets. Coils 520, 530 running across turning section magnets allows for two turning section magnets to be spatially positioned closer to each other due to the removal of the steric constraint of the turns, which reduces and/or minimizes the space 560 between two turning section magnets.

Figure 7:
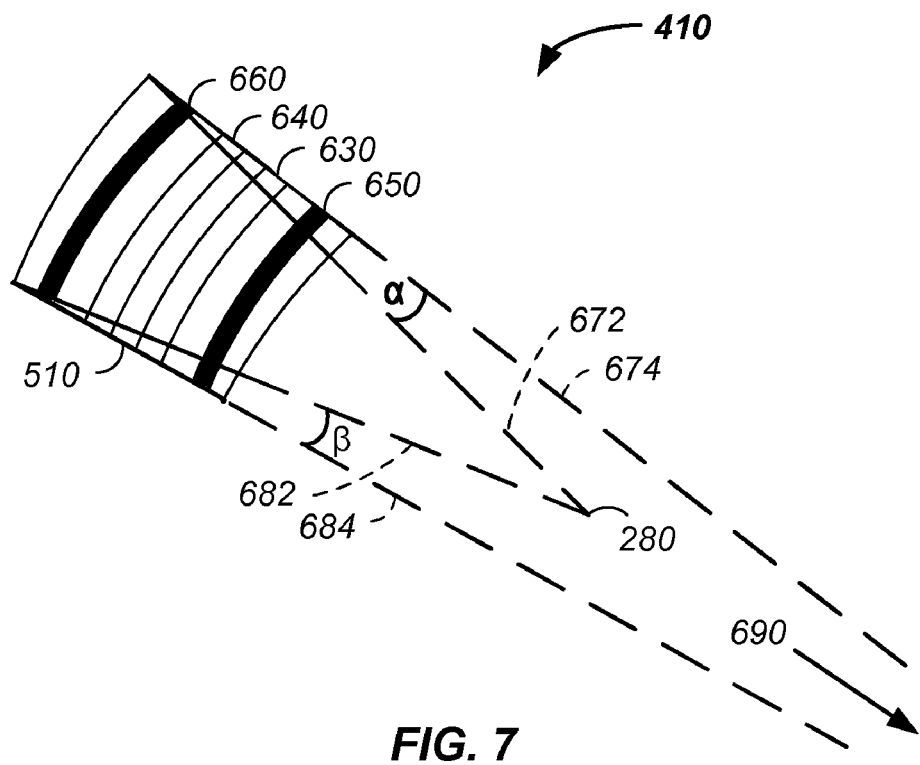
FIG. 7 illustrates a cross-sectional view of a turning magnet.
Figure 6:
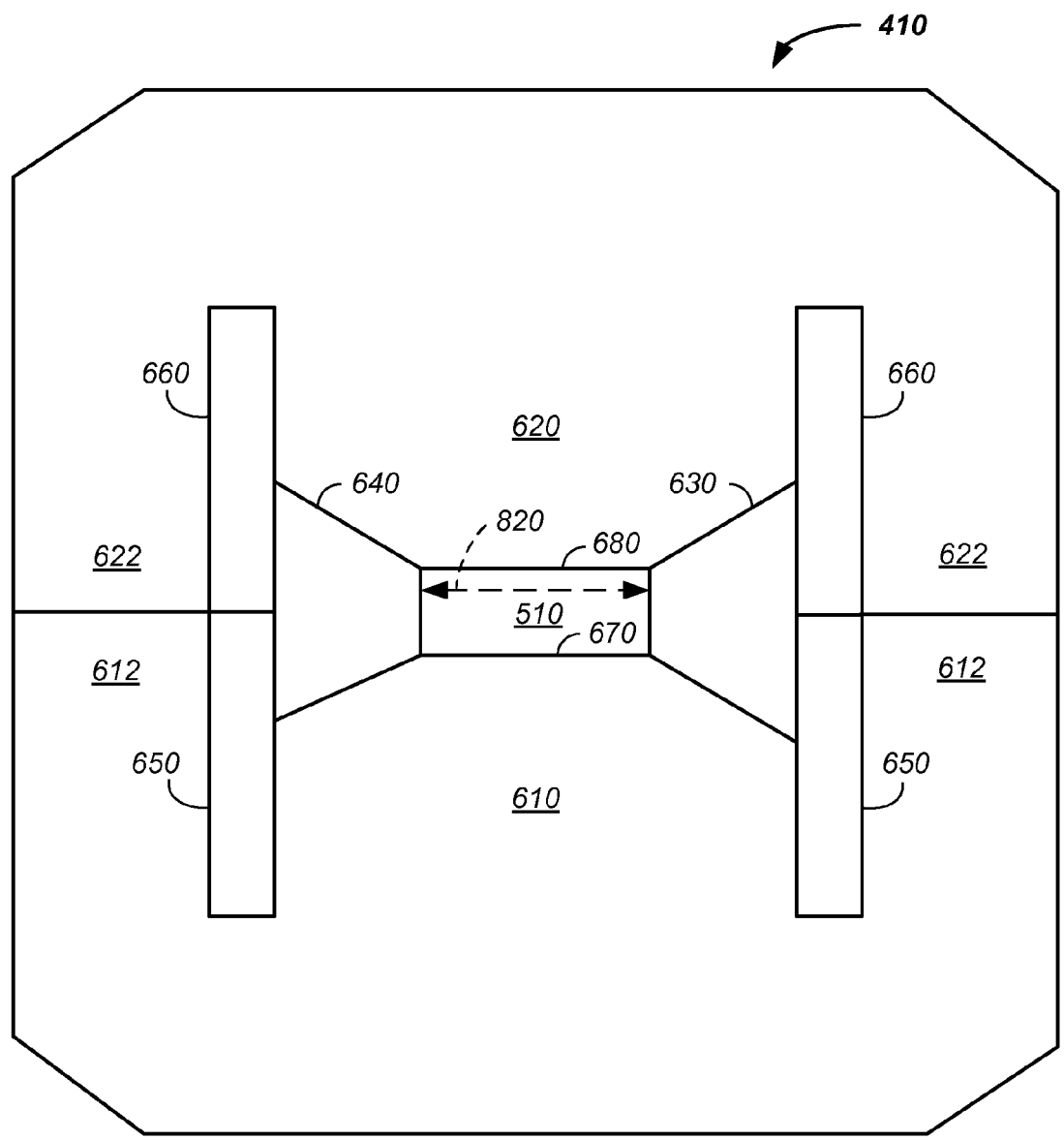
FIG. 6 illustrates a cross-sectional view of a turning magnet.
Figure 6:
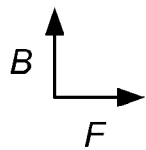

Referring now to FIGS. 6 and 7, two illustrative 90 degree rotated cross-sections of single magnet turning sections 410 are presented. The magnet assembly has a first magnet 610 and a second magnet 620. A magnetic field induced by coils, described infra, runs between the first magnet 610 to the second magnet 620 across the gap 510. Return magnetic fields run through a first yoke 612 and second yoke 622. The charged particles run through the vacuum tube in the gap. As illustrated, protons run into FIG. 6 through the gap 510 and the magnetic field, illustrated as vector B, applies a force F to the protons pushing the protons towards the center of the synchrotron, which is off page to the right in FIG. 6. The magnetic field is created using windings. A first coil makes up a first winding coil 650 and a second coil of wire makes up a second winding coil 660. Isolating gaps 630, 640, such as air gaps, isolate the iron based yokes 612, 622 from the gap 510. The gap is approximately flat to yield a uniform magnetic field across the gap, as described supra.

Referring again to FIG. 7, the ends of a single turning magnet are preferably beveled. Nearly perpendicular or right angle edges of a turning magnet 410 are represented by a dashed lines 674, 684. Preferably, the edge of the turning magnet is beveled at angles alpha, α, and beta, β, which is the off perpendicular angle between the right angles 674, 684 and beveled edges 672, 682. The angle alpha is used to describe the effect and the description of angle alpha applies to angle beta, but angle alpha is optionally different from angle beta. The angle alpha provides an edge focusing effect. Beveling the edge of the turning magnet 410 at angle alpha focuses the proton beam.

Multiple turning magnets provide multiple magnet edges that each have edge focusing effects in the synchrotron 310. If only one turning magnet is used, then the beam is only focused once for angle alpha or twice for angle alpha and angle beta. However, by using smaller turning magnets, more turning magnets fit into the turning sections 320 of the synchrotron 310. For example, if four magnets are used in a turning section 320 of the synchrotron, then there are eight possible edge focusing effect surfaces, two edges per magnet. The eight focusing surfaces yield a smaller cross-sectional beam size. This allows the use of a smaller gap 510.

The use of multiple edge focusing effects in the turning magnets results in not only a smaller gap, but also the use of smaller magnets and smaller power supplies. For a synchrotron 310 having four turning sections 320 where each turning sections has four turning magnets and each turning magnet has two focusing edges, a total of thirty-two focusing edges exist for each orbit of the protons in the circulating path of the synchrotron 310. Similarly, if 2, 6, or 8 magnets are used in a given turning section, or if 2, 3, 5, or 6 turning sections are used, then the number of edge focusing surfaces expands or contracts according to equation 2.

$$TFE = NTS * \frac{M}{NTS} * \frac{FE}{M} \quad \text{eq. 2}$$

where TFE is the number of total focusing edges, NTS is the number of turning section, M is the number of magnets, and FE is the number of focusing edges. Naturally, not all magnets are necessarily beveled and some magnets are optionally beveled on only one edge.

The inventors have determined that multiple smaller magnets have benefits over fewer larger magnets. For example, the use of 16 small magnets yields 32 focusing edges whereas the use of 4 larger magnets yields only 8 focusing edges. The use of a synchrotron having more focusing edges results in a circulating path of the synchrotron built without the use of focusing quadrupoles magnets. All prior art synchrotrons use quadrupoles in the circulating path of the synchrotron. Further, the use of quadrupoles in the circulating path necessitates additional straight sections in the circulating path of the synchrotron. Thus, the use of quadrupoles in the circulating path of a synchrotron results in synchrotrons having larger diameters or larger circumferences.

In various embodiments of the system described herein, the synchrotron has:
- at least 4 and preferably 6, 8, 10, or more edge focusing edges per 90 degrees of turn of the charged particle beam in a synchrotron having four turning sections;
- at least about 16 and preferably about 24, 32, or more edge focusing edges per orbit of the charged particle beam in the synchrotron;
- only 4 turning sections where each of the turning sections includes at least 4 and preferably 8 edge focusing edges;
- an equal number of straight sections and turning sections;
- exactly 4 turning sections;
- at least 4 edge focusing edges per turning section;
- no quadrupoles in the circulating path of the synchrotron;
- a rounded corner rectangular polygon configuration;
- a circumference of less than 60 meters;
- a circumference of less than 60 meters and 32 edge focusing surfaces; and/or
- any of about 8, 16, 24, or 32 non-quadrupole magnets per circulating path of the synchrotron, where the non-quadrupole magnets include edge focusing edges.

Referring now to FIG. 6, the incident magnetic field surface 670 of the first magnet 610 is further described. FIG. 6 is not to scale and is illustrative in nature. Local imperfections or unevenness in quality of the finish of the incident surface 670 results in inhomogeneities or imperfections in the magnetic field applied to the gap 510. Preferably, the incident surface 670 is flat, such as to within about a zero to three micron finish polish, or less preferably to about a ten micron finish polish.

Figure 8:
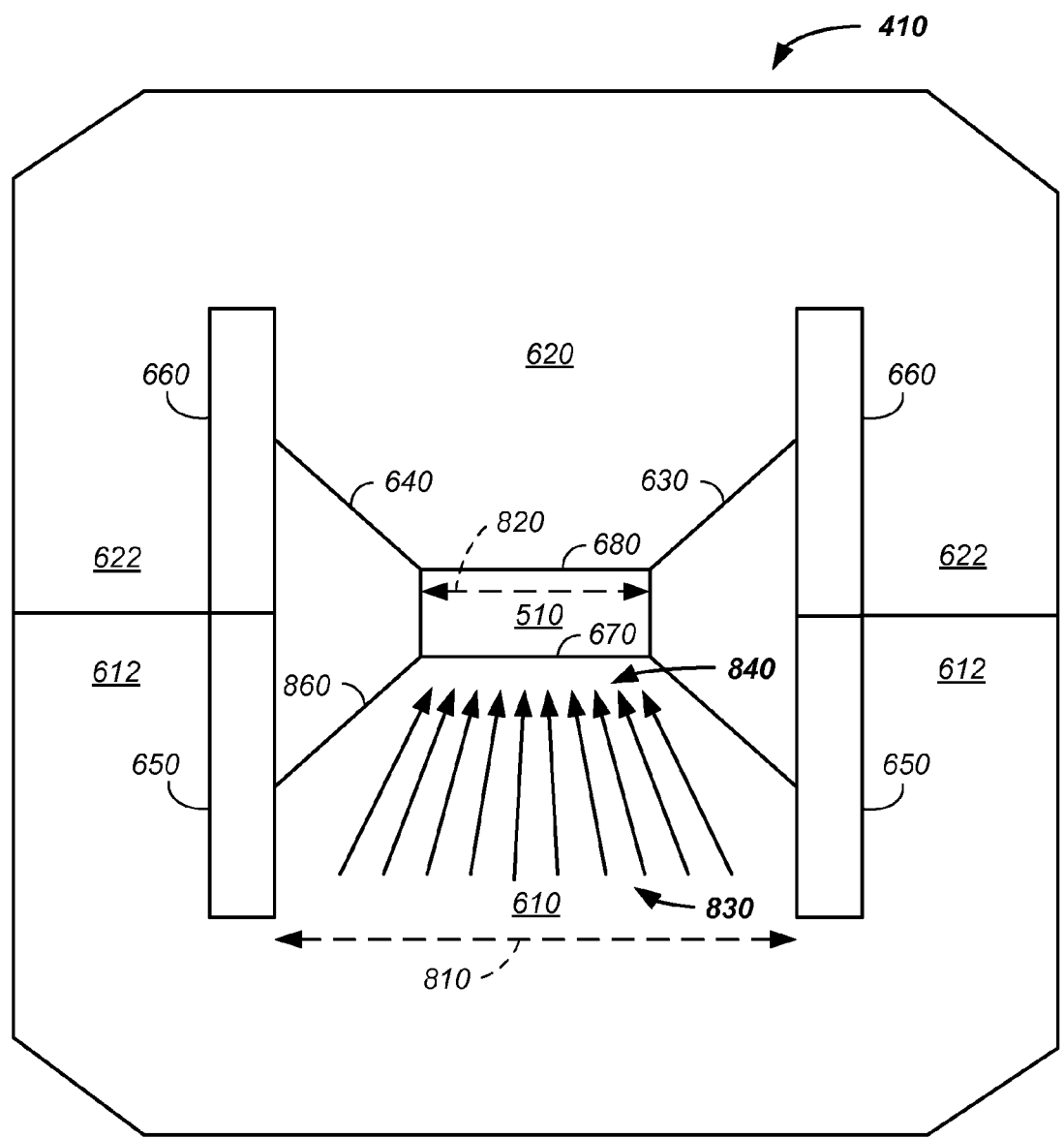
FIG. 8 illustrates magnetic field concentration in a turning magnet.

Referring now to FIG. 8, additional magnet elements, of the magnet cross-section illustratively represented in FIG. 6, are described. The first magnet 610 preferably contains an initial cross-sectional distance 810 of the iron based core. The contours of the magnetic field are shaped by the magnets 610, 620 and the yokes 612, 622. The iron based core tapers to a second cross-sectional distance 820. The magnetic field in the magnet preferentially stays in the iron based core as opposed to the gaps 630, 640. As the cross-sectional distance decreases from the initial cross-sectional distance 810 to the final cross-sectional distance 820, the magnetic field concentrates. The change in shape of the magnet from the longer distance 810 to the smaller distance 820 acts as an amplifier. The concentration of the magnetic field is illustrated by representing an initial density of magnetic field vectors 830 in the initial cross-section 810 to a concentrated density of magnetic field vectors 840 in the final cross-section 820. The concentration of the magnetic field due to the geometry of the turning magnets results in fewer winding coils 650, 660 being required and also a smaller power supply to the coils being required.

EXAMPLE I

In one example, the initial cross-section distance 810 is about fifteen centimeters and the final cross-section distance 820 is about ten centimeters. Using the provided numbers, the concentration of the magnetic field is about 15/10 or 1.5 times at the incident surface 670 of the gap 510, though the relationship is not linear. The taper 860 has a slope, such as about 20 to 60 degrees. The concentration of the magnetic field, such as by 1.5 times, leads to a corresponding decrease in power consumption requirements to the magnets.

Figure 9:
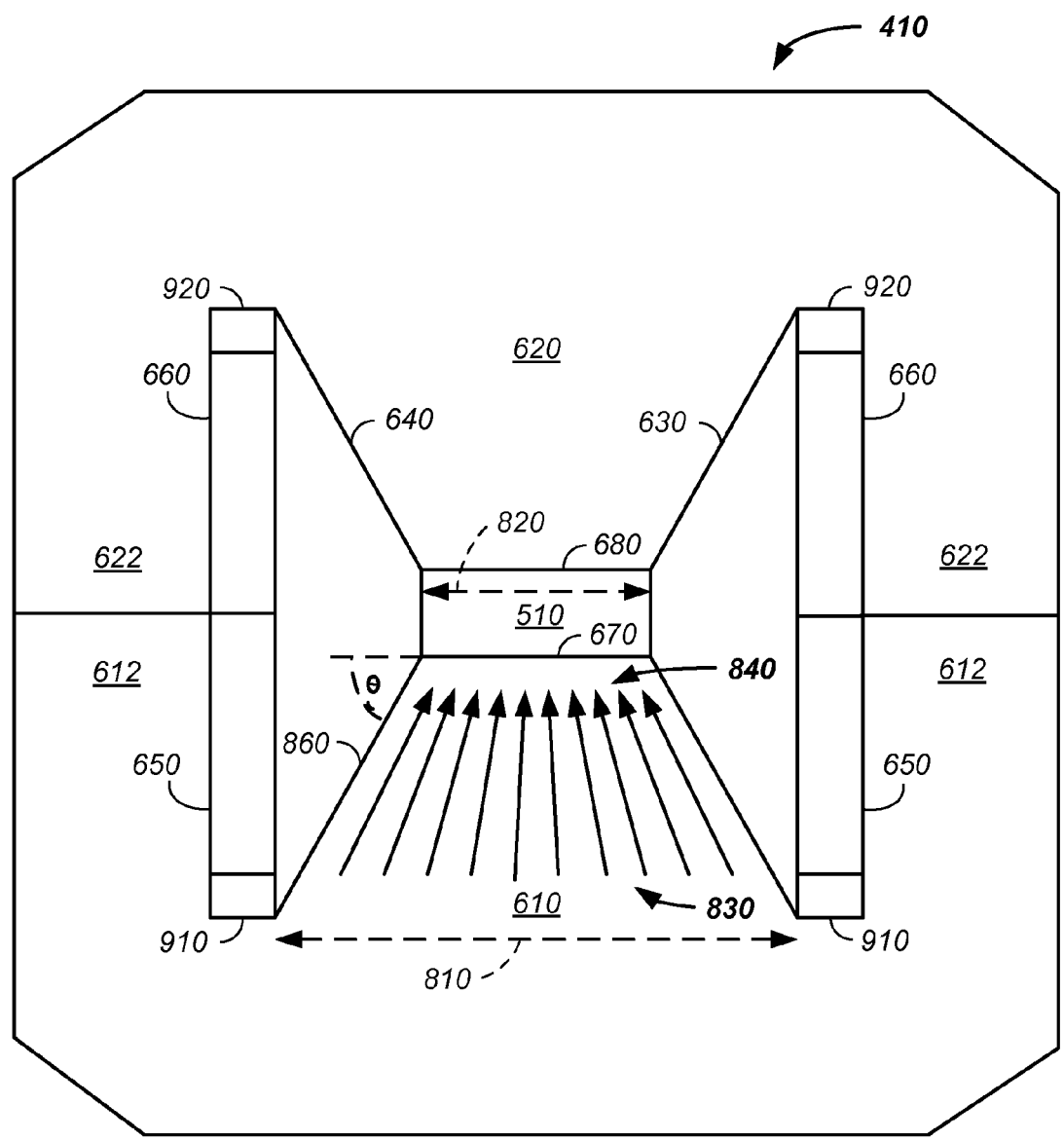
FIG. 9 illustrates correction coils in a turning magnet.

Referring now to FIG. 9, an additional example of geometry of the magnet used to concentrate the magnetic field is illustrated. As illustrated in FIG. 8, the first magnet 610 preferably contains an initial cross-sectional distance 810 of the iron based core. The contours of the magnetic field are shaped by the magnets 610, 620 and the yokes 612, 622. In this example, the core tapers to a second cross-sectional distance 820 with a smaller angle theta, θ. As described, supra, the magnetic field in the magnet preferentially stays in the iron based core as opposed to the gaps 630, 640. As the cross-sectional distance decreases from the initial cross-sectional distance 810 to the final cross-sectional distance 820, the magnetic field concentrates. The smaller angle, theta, results in a greater amplification of the magnetic field in going from the longer distance 810 to the smaller distance 820. The concentration of the magnetic field is illustrated by representing an initial density of magnetic field vectors 830 in the initial cross-section 810 to a concentrated density of magnetic field vectors 840 in the final cross-section 820. The concentration of the magnetic field due to the geometry of the turning magnets results in fewer winding coils 650, 660 being required and also a smaller power supply to the winding coils 650, 660 being required.

Still referring to FIG. 9, optional correction coils 910, 920 are illustrated that are used to correct the strength of one or more turning magnets. The correction coils 920, 930 supplement the winding coils 650, 660. The correction coils 910, 920 have correction coil power supplies that are separate from winding coil power supplies used with the winding coils 650, 660. The correction coil power supplies typically operate at a fraction of the power required compared to the winding coil power supplies, such as about 1, 2, 3, 5, 7, or 10 percent of the power and more preferably about 1 or 2 percent of the power used with the winding coils 650, 660. The smaller operating power applied to the correction coils 920, 920 allows for more accurate and/or precise control of the correction coils. The correction coils are used to adjust for imperfection in the turning magnets 410, 420, 430, 440.

Figure 10:
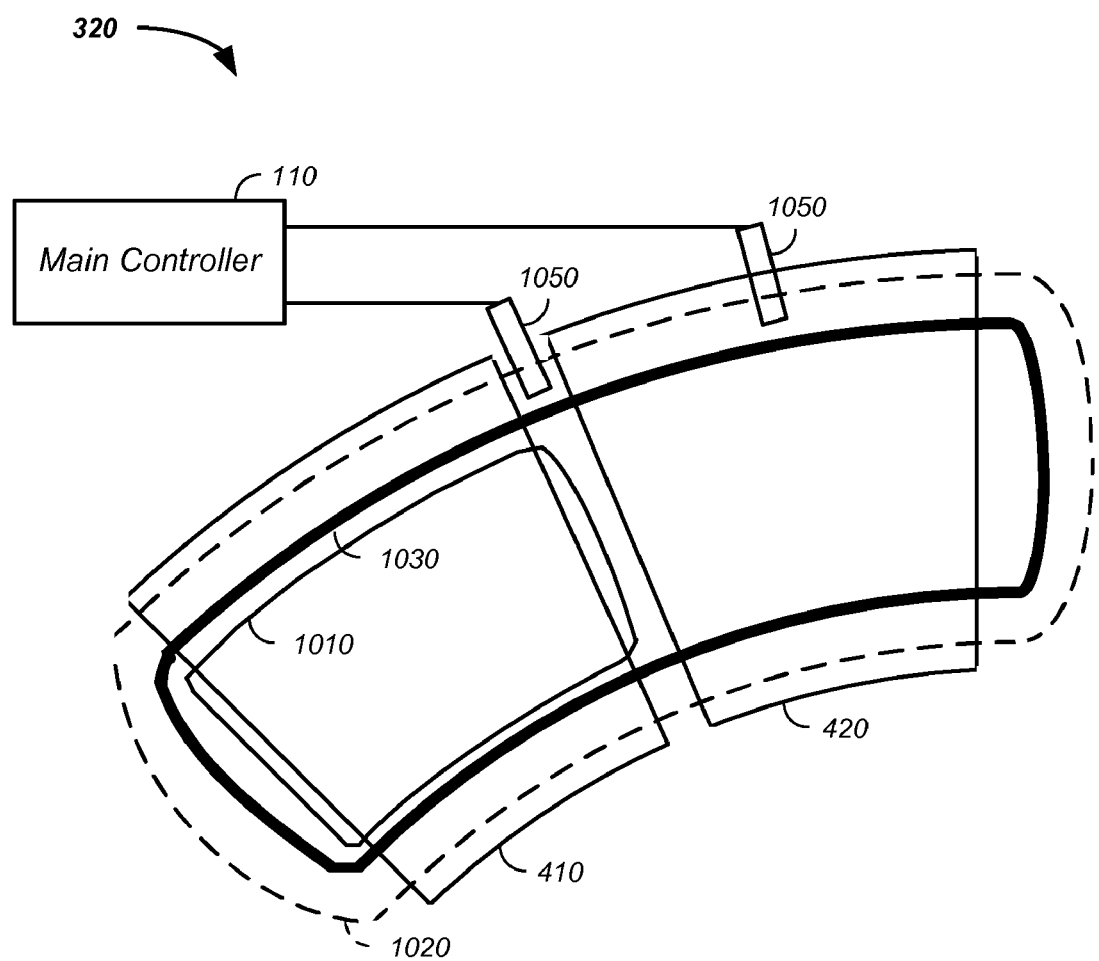
FIG. 10 illustrates a magnetic turning section of a synchrotron.

Referring now to FIG. 10, an example of winding coils and correction coils about a plurality of turning magnets 410, 420, 430, 440 in an ion beam turning section 320 is illustrated. One or more high precision magnetic field sensors are placed into the synchrotron and are used to measure the magnetic field at or near the proton beam path. For example, the magnetic sensors are optionally placed between turning magnets and/or within a turning magnet, such as at or near the gap or at or near the magnet core or yoke. The sensors are part of a feedback system to the correction coils. Thus, the system preferably stabilizes the magnetic field in the synchrotron elements rather that stabilizing the current applied to the magnets. Stabilization of the magnetic field allows the synchrotron to come to a new energy level quickly. This allows the system to be controlled to an operator or algorithm selected energy level with each pulse of the synchrotron and/or with each breath of the patient.

EXAMPLE II

Figure 11:
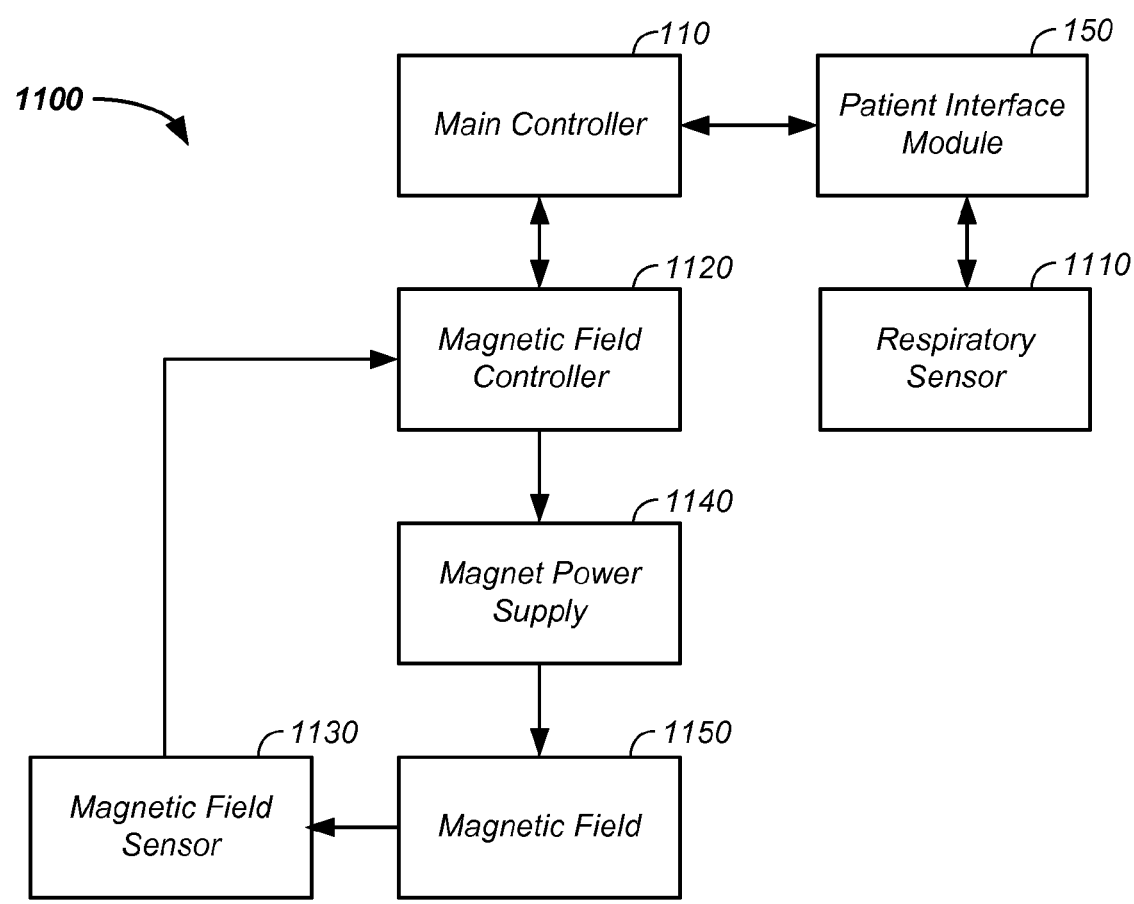
FIG. 11 illustrates a magnetic field control system.

Referring now to FIG. 11, an example is used to clarify the magnetic field control using a feedback loop 1100 to change delivery times and/or periods of proton pulse delivery. In one case, a respiratory sensor 1110 senses the breathing cycle of the subject. The respiratory sensor sends the information to an algorithm in a magnetic field controller 1120, typically via the patient interface module 150 and/or via the main controller 110 or a subcomponent thereof. The algorithm predicts and/or measures when the subject is at a particular point in the respiration cycle, such as at the top or bottom of a breath. Magnetic field sensors 1130, such as the high precision magnetic field sensors 1050, are used as input to the magnetic field controller, which controls a magnet power supply 1140 for a given magnetic field 1150, such as within a first turning magnet 410 of a synchrotron 130. The control feedback loop is thus used to dial the synchrotron to a selected energy level and deliver protons with the desired energy at a selected point in time, such as at the bottom of the breath. More particularly, the synchrotron accelerates the protons and the control feedback loop keeps the protons in the circulating path by synchronously adjusting the magnetic field strength of the turning magnets. Intensity of the proton beam is also selectable at this stage. The feedback control to the correction coils allows rapid selection of energy levels of the synchrotron that are tied to the patient's respiration cycle. This system is in stark contrast to a system where the current is stabilized and the synchrotron deliver pulses with a period, such as 10 or 20 cycles second with a fixed period.

The feedback or the magnetic field design coupled with the correction coils allows for the extraction cycle to match the varying respiratory rate of the patient.

Traditional extraction systems do not allow this control as magnets have memories in terms of both magnitude and amplitude of a sine wave. Hence, in a traditional system, in order to change frequency, slow changes in current must be used. However, with the use of the feedback loop using the magnetic field sensors, the frequency and energy level of the synchrotron are rapidly adjustable. Further aiding this process is the use of a novel extraction system that allows for acceleration of the protons during the extraction process, described infra.

EXAMPLE III

Referring again to FIG. 10, an example of a winding coil 1030 that covers four turning magnets 410, 420, 430, 440 is provided. As described, supra, this system reduces space between turning section allowing more magnetic field to be applied per radian of turn. A first correction coil 1010 is illustrated that is used to correct the magnetic field for the first turning magnet 410. Individual correction coils for each turning magnet are preferred and individual correction coils yield the most precise and/or accurate magnetic field in each turning section magnet. Particularly, the individual correction coil 1010 is used to compensate for imperfections in the individual magnet of a given turning section. Hence, with a series of magnetic field sensors, corresponding magnetic fields are individually adjustable in a series of feedback loops, via a magnetic field monitoring system 1030, as an independent coil is used for each turning section. Alternatively, a multiple magnet correction coil 1020 is used to correct the magnetic field for a plurality of turning section magnets.

Flat Gap Surface

While the gap surface is described in terms of the first turning magnet 410, the discussion applies to each of the turning magnets in the synchrotron. Similarly, while the gap 510 surface is described in terms of the magnetic field incident surface 670, the discussion additionally optionally applies to the magnetic field exiting surface 680.

The magnetic field incident surface 670 of the first magnet 610 is preferably about flat, such as to within about a zero to three micron finish polish or less preferably to about a ten micron finish polish. By being very flat, the polished surface spreads the unevenness of the applied magnetic field across the gap 510. The very flat surface, such as about 0, 1, 2, 4, 6, 8, 10, 15, or 20 micron finish, allows for a smaller gap size, a smaller applied magnetic field, smaller power supplies, and tighter control of the proton beam cross-sectional area.

Proton Beam Extraction

Figure 12:
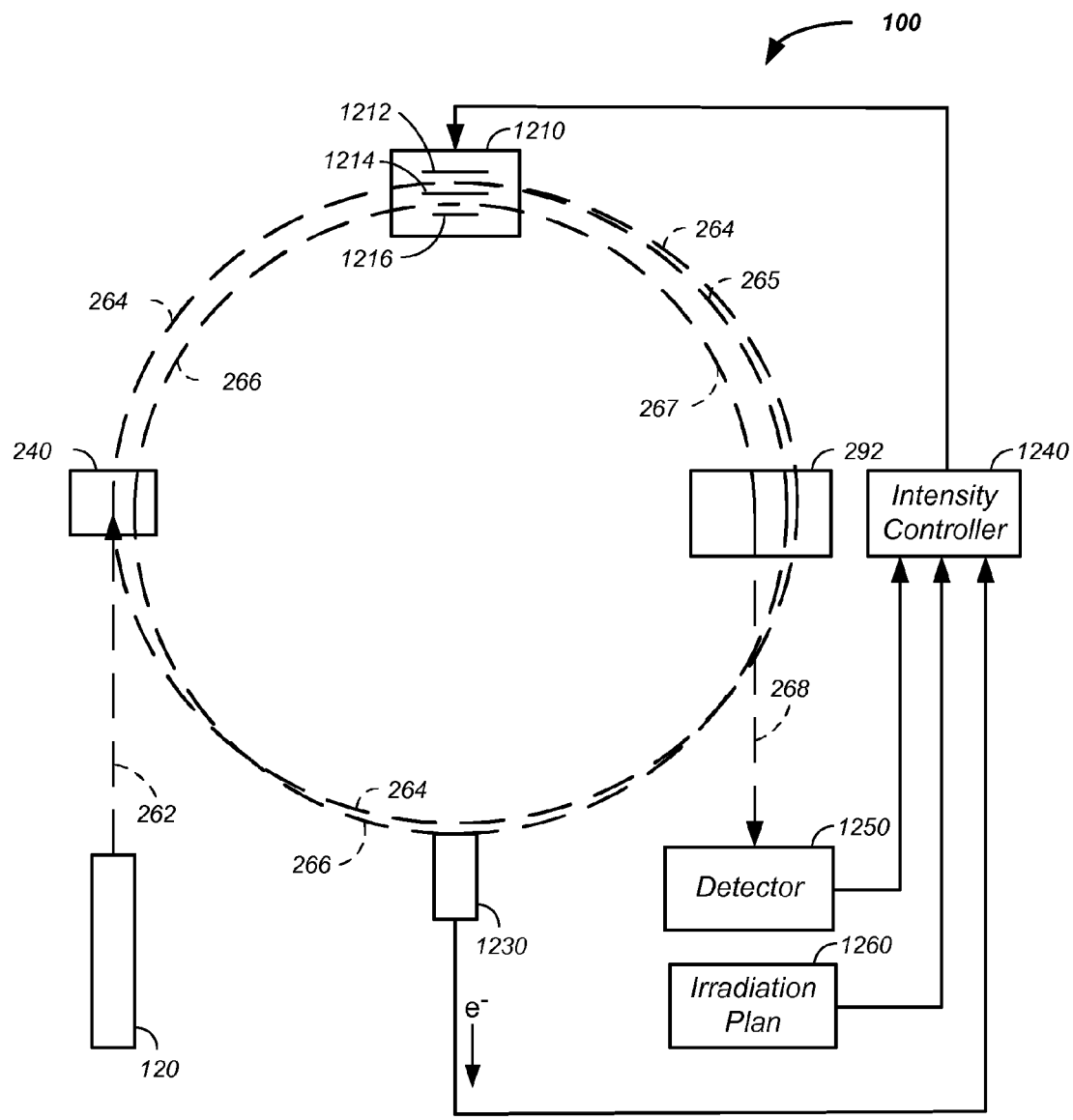
FIG. 12 illustrates a charged particle extraction and intensity control system.

Referring now to FIG. 12, an exemplary proton extraction process from the synchrotron 130 is illustrated. For clarity, FIG. 12 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path 264, which is maintained with a plurality of turning magnets 250. The circulating path is referred to herein as an original central beamline 264. The protons repeatedly cycle around a central point in the synchrotron 280. The proton path traverses through an RF cavity system 1210. To initiate extraction, an RF field is applied across a first blade 1212 and a second blade 1214, in the RF cavity system 1210. The first blade 1212 and second blade 1214 are referred to herein as a first pair of blades.

In the proton extraction process, a radio-frequency (RF) voltage is applied across the first pair of blades, where the first blade 1212 of the first pair of blades is on one side of the circulating proton beam path 264 and the second blade 1214 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The applied RF field is timed to apply outward or inward movement to a given band of protons circulating in the synchrotron accelerator. Each orbit of the protons is slightly more off axis compared to the original circulating beam path 264. Successive passes of the protons through the RF cavity system are forced further and further from the original central beamline 264 by altering the direction and/or intensity of the RF field with each successive pass of the proton beam through the RF field.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the effect of the approximately 1000 changing beam paths with each successive path of a given band of protons through the RF field are illustrated as the altered beam path 265.

With a sufficient sine wave betatron amplitude, the altered circulating beam path 265 touches a material 1230, such as a foil or a sheet of foil. The foil is preferably a lightweight material, such as beryllium, a lithium hydride, a carbon sheet, or a material of low nuclear charge. A material of low nuclear charge is a material composed of atoms consisting essentially of atoms having six or fewer protons. The foil is preferably about 10 to 150 microns thick, is more preferably 30 to 100 microns thick, and is still more preferably 40-60 microns thick. In one example, the foil is beryllium with a thickness of about 50 microns. When the protons traverse through the foil, energy of the protons is lost and the speed of the protons is reduced. Typically, a current is also generated, described infra. Protons moving at a slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 1230 is optionally adjusted to created a change in the radius of curvature, such as about ½, 1, 2, 3, or 4 mm less than the last pass of the protons 265 or original radius of curvature 264. Protons moving with the smaller radius of curvature travel between a second pair of blades. In one case, the second pair of blades is physically distinct and/or are separated from the first pair of blades. In a second case, one of the first pair of blades is also a member of the second pair of blades. For example, the second pair of blades is the second blade 1214 and a third blade 1216 in the RF cavity system 1210. A high voltage DC signal, such as about 1 to 5 kV, is then applied across the second pair of blades, which directs the protons out of the synchrotron through a deflector 292, such as a Lamberson magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

Because the extraction system does not depend on any change any change in magnetic field properties, it allows the synchrotron to continue to operate in acceleration or deceleration mode during the extraction process. Stated differently, the extraction process does not interfere with synchrotron. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time.

Charged Particle Beam Intensity Control

Control of applied field, such as a radio-frequency (RF) field, frequency and magnitude in the RF cavity system 1210 allows for intensity control of the extracted proton beam, where intensity is extracted proton flux per unit time or the number of protons extracted as a function of time.

Referring still to FIG. 12, when protons in the proton beam hit the material 1230 electrons are given off resulting in a current. The resulting current is converted to a voltage and is used as part of a ion beam intensity monitoring system or as part of an ion beam feedback loop for controlling beam intensity. The voltage is optionally measured and sent to the main controller 110 or to a controller subsystem, such as an intensity controller 1240. More particularly, when protons in the charged particle beam path pass through the material 1230, some of the protons lose a small fraction of their energy, such as about one-tenth of a percent, which results in a secondary electron. That is, protons in the charged particle beam push some electrons when passing through material 1230 giving the electrons enough energy to cause secondary emission. The resulting electron flow results in a current or signal that is proportional to the number of protons going through the target material 1230. The resulting current is preferably converted to voltage and amplified. The resulting signal is referred to as a measured intensity signal.

The amplified signal or measured intensity signal resulting from the protons passing through the material 1230 is preferably used in controlling the intensity of the extracted protons. For example, the measured intensity signal is compared to a goal signal, which is predetermined in an irradiation of the tumor plan. The difference between the measured intensity signal and the planned for goal signal is calculated. The difference is used as a control to the RF generator. Hence, the measured flow of current resulting from the protons passing through the material 1230 is used as a control in the RF generator to increase or decrease the number of protons undergoing betatron oscillation and striking the material 1230. Hence, the voltage determined off of the material 1230 is used as a measure of the orbital path and is used as a feedback control to control the RF cavity system. Alternatively, the measured intensity signal is not used in the feedback control and is just used as a monitor of the intensity of the extracted protons.

As described, supra, the photons striking the material 1230 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable.

For example, protons initially move at an equilibrium trajectory in the synchrotron 130. An RF field is used to excite the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude, RF frequency, or RF field. Preferably, the measured intensity signal is compared to a target signal and a measure of the difference between the measured intensity signal and target signal is used to adjust the applied RF field in the RF cavity system 1210 in the extraction system to control the intensity of the protons in the extraction step. Stated again, the signal resulting from the protons striking and/or passing through the material 130 is used as an input in RF field modulation. An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector external to the synchrotron 130 is used to determine the flux of protons extracted from the synchrotron and a signal from the external detector is used to alter the RF field or RF modulation in the RF cavity system 1210. Here the external detector generates an external signal, which is used in a manner similar to the measured intensity signal, described in the preceding paragraphs.

In yet another example, when a current from material 130 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

In yet still an additional embodiment, a method or apparatus for extracting intensity controlled charged particles from charged particles circulating in a synchrotron of a charged particle cancer therapy system, includes: oscillation blades with a radio-frequency voltage across the for inducing oscillating charged particles from the charged particles circulating in the synchrotron; an extraction material where the oscillating charged particles traverse the extraction material during use generating both reduced energy charged particles and secondary emission electrons or a current; and extraction blades used in extracting the energy controlled and intensity controlled charged particles from the synchrotron. Preferably, the system includes a feedback intensity controller that generates a measure of the secondary emission electrons, compares the measure and a target signal, such as an irradiation plan signal 1260 for each beam position striking the tumor 1520, and having the intensity controller adjusts amplitude of the radio-frequency voltage based on the comparison yielding intensity controlled and energy controlled extracted charged particles. The beam intensity is optionally measured with a detector 1250 after extraction from the synchrotron.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller simultaneously controls the intensity control system to yield an extracted proton beam with controlled energy and controlled intensity where the controlled energy and controlled intensity are independently variable. Thus the irradiation spot hitting the tumor is under independent control of:

time;

energy;

intensity;

x-axis position, where the x-axis represents horizontal movement of the proton beam relative to the patient, and y-axis position, where the y-axis represents vertical movement of the proton beam relative to the patient.

In addition, the patient is optionally independently rotated relative to a translational axis of the proton beam at the same time.

Proton Beam Position Control

Figure 13:
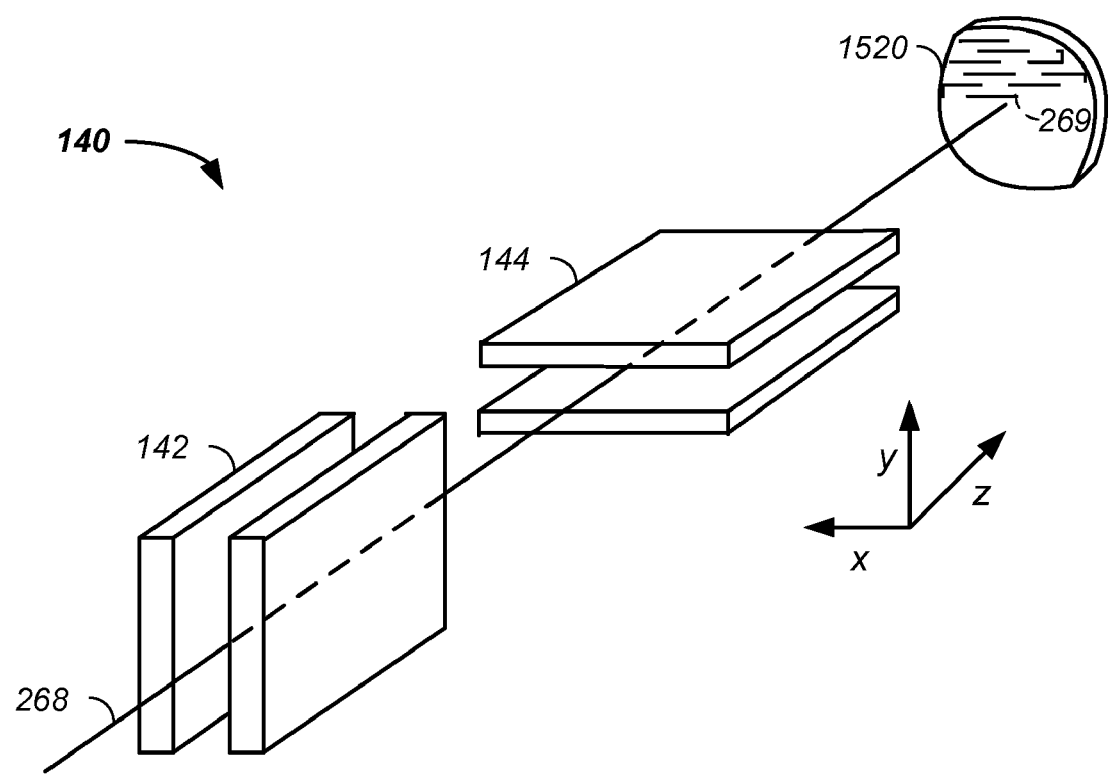
FIG. 13 illustrates 3-dimensional scanning of a proton beam focal spot.

Referring now to FIG. 13, a beam delivery and tissue volume scanning system is illustrated. Presently, the worldwide radiotherapy community uses a method of dose field forming using a pencil beam scanning system. In stark contrast, FIG. 13 illustrates a spot scanning system or tissue volume scanning system. In the tissue volume scanning system, the proton beam is controlled, in terms of transportation and distribution, using an inexpensive and precise scanning system. The scanning system is an active system, where the beam is focused into a spot focal point of about one-half, one, two, or three millimeters in diameter. The focal point is translated along two axes while simultaneously altering the applied energy of the proton beam, which effectively changes the third dimension of the focal point. For example, in the illustrated system in FIG. 13, the spot is translated up a vertical axis, is moved horizontally, and is then translated down a vertical axis. In this example, current is used to control a vertical scanning system having at least one magnet. The applied current alters the magnetic field of the vertical scanning system to control the vertical deflection of the proton beam. Similarly, a horizontal scanning magnet system controls the horizontal deflection of the proton beam. The degree of transport along each axes is controlled to conform to the tumor cross-section at the given depth. The depth is controlled by changing the energy of the proton beam. For example, the proton beam energy is decreased, so as to define a new penetration depth, and the scanning process is repeated along the horizontal and vertical axes covering a new cross-sectional area of the tumor. Combined, the three axes of control allow scanning or movement of the proton beam focal point over the entire volume of the cancerous tumor. The time at each spot and the direction into the body for each spot is controlled to yield the desired radiation does at each sub-volume of the cancerous volume while distributing energy hitting outside of the tumor.

The focused beam spot volume dimension is preferably tightly controlled to a diameter of about 0.5, 1, or 2 millimeters, but is alternatively several centimeters in diameter. Preferred design controls allow scanning in two directions with: (1) a vertical amplitude of about 100 mm amplitude and frequency up to 200 Hz; and (2) a horizontal amplitude of about 700 mm amplitude and frequency up to 1 Hz. More or less amplitude in each axis is possible by altering the scanning magnet systems.

In FIG. 13, the proton beam goes along a z-axis controlled by the beam energy, the horizontal movement is along an x-axis, and the vertical direction is along a y-axis. The distance the protons move along the z-axis into the tissue, in this example, is controlled by the kinetic energy of the proton. This coordinate system is arbitrary and exemplary. The actual control of the proton beam is controlled in 3-dimensional space using two scanning magnet systems and by controlling the kinetic energy of the proton beam. The use of the extraction system, described supra, allows for different scanning patterns. Particularly, the system allows simultaneous adjustment of the x-, y-, and z-axes in the irradiation of the solid tumor. Stated again, instead of scanning along an x,y-plane and then adjusting energy of the protons, such as with a range modulation wheel, the system allows for moving along the z-axes while simultaneously adjusting the x- and or y-axes. Hence, rather than irradiating slices of the tumor, the tumor is optionally irradiated in three simultaneous dimensions. For example, the tumor is irradiated around an outer edge of the tumor in three dimensions. Then the tumor is irradiated around an outer edge of an internal section of the tumor. This process is repeated until the entire tumor is irradiated. The outer edge irradiation is preferably coupled with simultaneous rotation of the subject, such as about a vertical y-axis. This system allows for maximum efficiency of deposition of protons to the tumor, as defined using the Bragg peak, to the tumor itself with minimal delivery of proton energy to surrounding healthy tissue.

Combined, the system allows for multi-axes control of the charged particle beam system in a small space with low power supply. For example, the system uses multiple magnets where each magnet has at least one edge focusing effect in each turning section of the synchrotron and/or multiple magnets having concentrating magnetic field geometry, as described supra. The multiple edge focusing effects in the circulating beam path of the synchrotron combined with the concentration geometry of the magnets and described extraction system yields a synchrotron having:

a small circumference system, such as less than about 50 meters;

a vertical proton beam size gap of about 2 cm;

corresponding reduced power supply requirements associated with the reduced gap size;

an extraction system not requiring a newly introduced magnetic field;

acceleration or deceleration of the protons during extraction; and control of z-axis energy during extraction.

The result is a 3-dimensional scanning system, x-, y-, and z-axes control, where the z-axes control resides in the synchrotron and where the z-axes energy is variably controlled during the extraction process inside the synchrotron.

Figure 14:
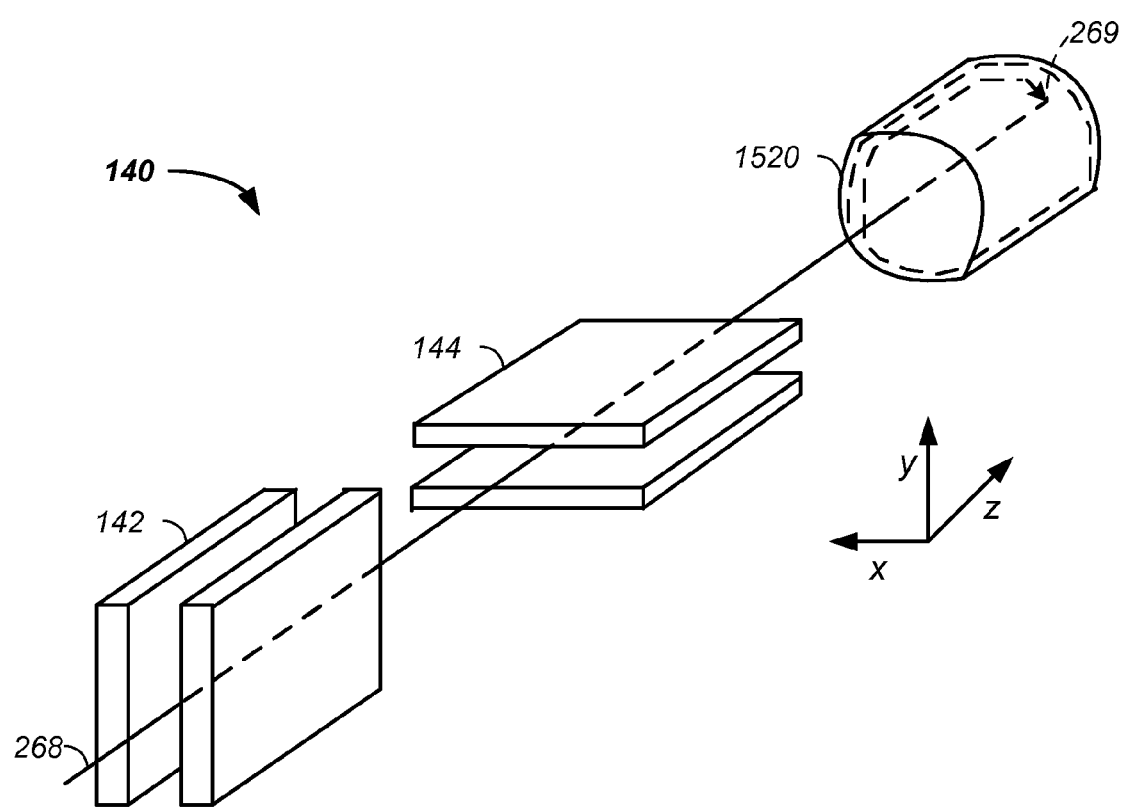
FIG. 14 illustrates 4- or 5-dimensional scanning of a charged particle beam spot.

Referring now to FIG. 14, an example of a targeting system 140 used to direct the protons to the tumor with 4-dimensional scanning control is provided, where the 4-dimensional scanning control is along the x-, y-, and z-axes along with intensity control, as described supra. Typically, charged particles traveling along the transport path 268 are directed through a first axis control element 142, such as a vertical control, and a second axis control element 144, such as a horizontal control and into a tumor 1520. As described, supra, the extraction system also allows for simultaneous variation in the z-axis. Further, as describe, supra, the intensity or dose of the extracted beam is optionally simultaneously and independently controlled and varied. Thus instead of irradiating a slice of the tumor, as in FIG. 13, all four dimensions defining the targeting spot of the proton delivery in the tumor are simultaneously variable. The simultaneous variation of the proton delivery spot is illustrated in FIG. 14 by the spot delivery path 269. In the illustrated case, the protons are initially directed around an outer edge of the tumor and are then directed around an inner radius of the tumor. Combined with rotation of the subject about a vertical axis, a multi-field illumination process is used where a not yet irradiated portion of the tumor is preferably irradiated at the further distance of the tumor from the proton entry point into the body. This yields the greatest percentage of the proton delivery, as defined by the Bragg peak, into the tumor and minimizes damage to peripheral healthy tissue.

Imaging System

Herein, an X-ray system is used to illustrate an imaging system.

Timing

An X-ray is preferably collected either (1) just before or (2) concurrently with treating a subject with proton therapy for a couple of reasons.

First, movement of the body, described supra, changes the local position of the tumor in the body relative to other body constituents. If the subject has an X-ray taken and is then bodily moved to a proton treatment room, accurate alignment of the proton beam to the tumor is problematic. Alignment of the proton beam to the tumor using one or more X-rays is best performed at the time of proton delivery or in the seconds or minutes immediately prior to proton delivery and after the patient is placed into a therapeutic body position, which is typically a fixed position or partially immobilized position.

Second, the X-ray taken after positioning the patient is used for verification of proton beam alignment to a targeted position, such as a tumor and/or internal organ position.

Positioning

An X-ray is preferably taken just before treating the subject to aid in patient positioning. For positioning purposes, an X-ray of a large body area is not needed. In one embodiment, an X-ray of only a local area is collected. When collecting an X-ray, the X-ray has an X-ray path. The proton beam has a proton beam path. Overlaying the X-ray path with the proton beam path is one method of aligning the proton beam to the tumor. However, this method involves putting the X-ray equipment into the proton beam path, taking the X-ray, and then moving the X-ray equipment out of the beam path. This process takes time. The elapsed time while the X-ray equipment moves has a couple of detrimental effects. First, during the time required to move the X-ray equipment, the body moves. The resulting movement decreases precision and/or accuracy of subsequent proton beam alignment to the tumor. Second, the time require to move the X-ray equipment is time that the proton beam therapy system is not in use, which decreases the total efficiency of the proton beam therapy system.

Figure 15:
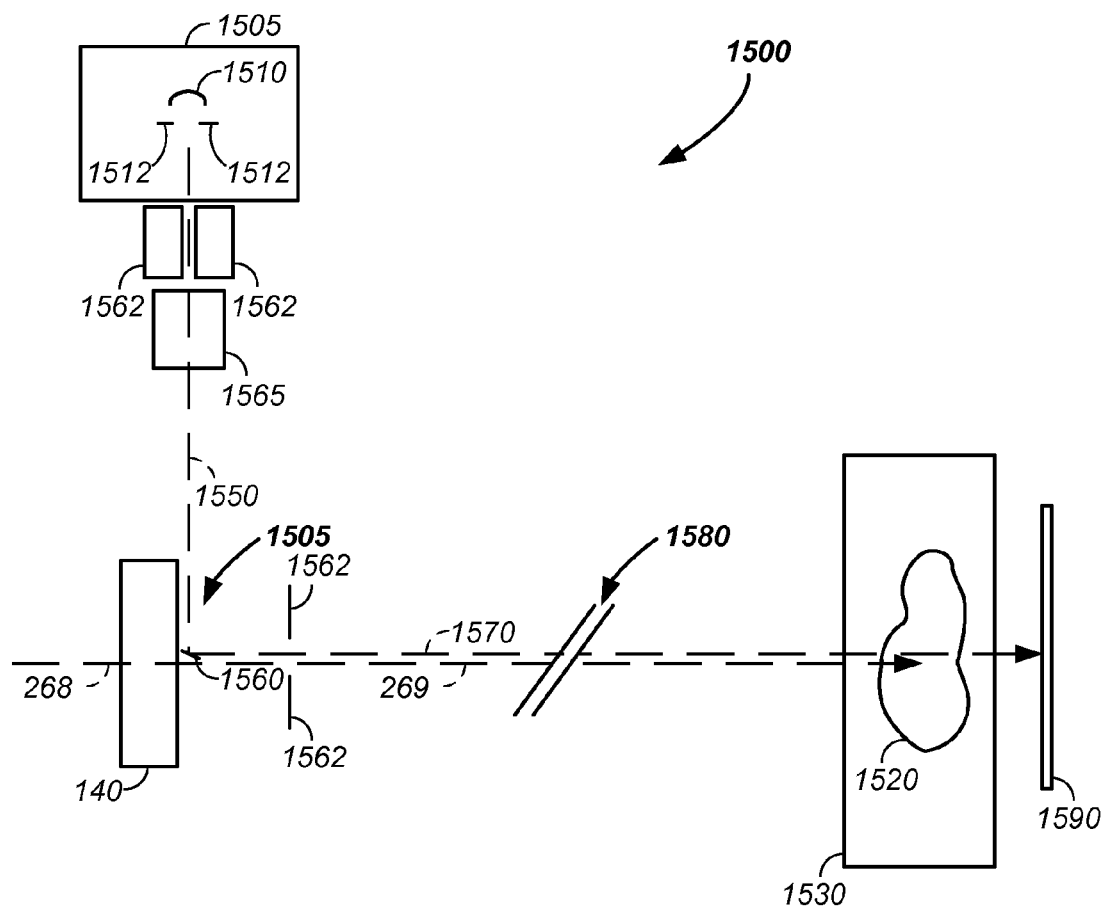
FIG. 15 illustrates an X-ray source proximate a particle beam path.

Referring now to FIG. 15, in one embodiment, an X-ray is generated close to, but not in, the proton beam path. A proton beam therapy system and an X-ray system combination 1500 is illustrated in FIG. 15. The proton beam therapy system has a proton beam 268 in a transport system after the deflector 292 of the synchrotron 130. The proton beam is directed by the targeting/delivery system 140 to a tumor 1520 of a patient 1530. The X-ray system 1505 includes an electron beam source 1540 generating an electron beam 1550. The electron beam is directed to an X-ray generation source 1560, such as a piece of tungsten. Preferably, the tungsten X-ray source is located about 1, 2, 3, 5, 10, 15, or 20 millimeters from the proton beam path 268. When the electron beam 1550 hits the tungsten, X-rays are generated in all directions. X-rays are blocked with a port 1562 and are selected for an X-ray beam path 1570. The X-ray beam path 1570 and proton beam path 260 run substantially in parallel as they progress to the tumor 1520. The distance between the X-ray beam path 1570 and proton beam path 269 preferably diminishes to near zero and/or the X-ray beam path 1570 and proton beam path 269 overlap by the time they reach the tumor 1520. Simple geometry shows this to be the case given the long distance, of at least a meter, between the tungsten and the tumor 1520. The distance is illustrated as a gap 1580 in FIG. 15. The X-rays are detected at an X-ray detector 1590, which is used to form an image of the tumor 1520 and/or position of the patient 1530.

Referring now to FIG. 15, an example of an X-ray generation device 1500 having an enhanced lifetime is provided. Electrons are generated at a cathode 1510, focused with a control electrode 1512, and accelerated with a series of accelerating electrodes 1562 and focused with focusing electrodes 1565. The accelerated electrons 1550 impact an X-ray generation source 1560 resulting in generated X-rays that are then directed along an X-ray path 1570 to the subject 1530. The concentrating of the electrons from a first diameter of the cathode to a second diameter of the accelerated electrons 1550 allows the cathode to operate at a reduced temperature and still yield the necessary amplified level of electrons at the X-ray generation source 1560. In one example, the X-ray generation source 1560 is the anode coupled with the cathode 1510 and/or the X-ray generation source is substantially composed of tungsten.

As a whole, the system generates an X-ray beam that lies in substantially the same path as the proton therapy beam. The X-ray beam is generated by striking a tungsten or equivalent material with an electron beam. The X-ray generation source is located proximate to the proton beam path. Geometry of the incident electrons, geometry of the X-ray generation material, and geometry of the X-ray beam blocker 262 yield an X-ray beam that runs either in substantially in parallel with the proton beam or results in an X-ray beam path that starts proximate the proton beam path an expands to cover and transmit through a tumor cross-sectional area to strike an X-ray detector array or film allowing imaging of the tumor from a direction and alignment of the proton therapy beam. The X-ray image is then used to control the charged particle beam path to accurately and precisely target the tumor, and/or is used in system verification and validation.

Patient Immobilization

Accurate and precise delivery of a proton beam to a tumor of a patient requires: (1) positioning control of the proton beam and (2) positioning control of the patient. As described, supra, the proton beam is controlled using algorithms and magnetic fields to a diameter of about 0.5, 1, or 2 millimeters. This section addresses partial immobilization, restraint, and/or alignment of the patient to insure the tightly controlled proton beam efficiently hits a target tumor and not surrounding healthy tissue as a result of patient movement.

In this section an x-, y-, and z-axes coordinate system and rotation axis is used to describe the orientation of the patient relative to the proton beam. The z-axis represent travel of the proton beam, such as the depth of the proton beam into the patient. When looking at the patient down the z-axis of travel of the proton beam, the x-axis refers to moving left or right across the patient and the y-axis refers to movement up or down the patient. A first rotation axis is rotation of the patient about the y-axis and is referred to herein as a rotation axis, platform 1612 rotation axis, or y-axis of rotation. In addition, tilt is rotation about the x-axis, yaw is rotation about the y-axis, and roll is rotation about the z-axis. In this coordinate system, the proton beam path 269 optionally runs in any direction. As an illustrative matter, the proton beam path running through a treatment room is described as running horizontally through the treatment room.

In this section, three examples of positioning are provided: (1) a semi-vertical partial immobilization system; (2) a sitting partial immobilization system; and (3) a laying position. Elements described for one immobilization apply to other immobilization systems with small changes. For example, a head rest will adjust along one axis for a reclined position, along a second axis for a seated position, and along a third axis for a laying position. However, the headrest itself is similar for each immobilization position.

Vertical Patient Positioning/Immobilization

Figure 16:
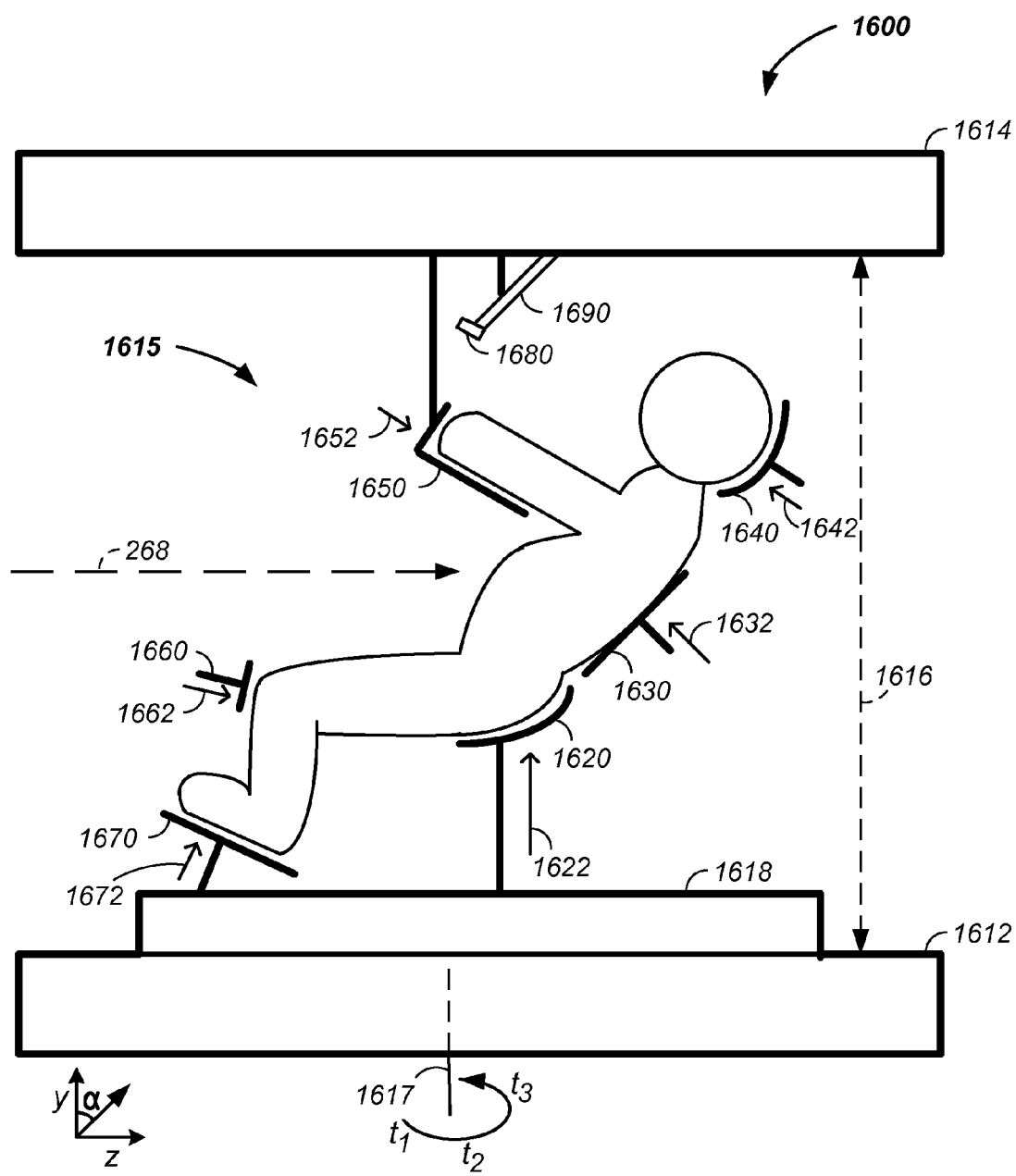
FIG. 16 illustrates a semi-vertical patient positioning system.

Referring now to FIG. 16, a semi-vertical patient positioning and/or partial immobilization system 1600 is described. The semi-vertical patient positioning system 1600 is preferably used in conjunction with proton therapy of tumors in the torso. The patient positioning and/or immobilization system 1600 controls and/or restricts movement of the patient during proton beam therapy. In a first partial immobilization embodiment, the patient is positioned in a semi-vertical position in a proton beam therapy system. As illustrated, the patient is reclining at an angle alpha, $\alpha$, about 45 degrees off of the y-axis as defined by an axis running from head to foot of the patient. More generally, the patient is optionally completely standing in a vertical position of zero degrees off the of y-axis or is in a semi-vertical position alpha that is reclined about 5, 10, 15, 20, 25, 30, 35, 40, 45, 50, 55, 60, or 65 degrees off of the y-axis toward the z-axis.

Still referring to FIG. 16, patient positioning constraints 1615 are used to maintain the patient in a treatment position, including one or more of: a seat support 1620, a back support 1630, a head support 1640, an arm support 1650, a knee support 1660, and a foot support 1670. The constraints are optionally and independently rigid or semi-rigid. Examples of a semi-rigid material include a high or low density foam or a visco-elastic foam. For example the foot support 1670 is preferably rigid and the back support 1630 is preferably semi-rigid, such as a high density foam material. One or more of the positioning constraints 1615 are movable and/or under computer control for rapid positioning and/or immobilization of the patient. For example, the seat support 1620 is adjustable along a seat adjustment axis 1622, which is preferably the y-axis; the back support 1630 is adjustable along a back support axis 1632, which is preferably dominated by z-axis movement with a y-axis element; the head support 1640 is adjustable along a head support axis 1642, which is preferably dominated by z-axis movement with a y-axis element; the arm support 1650 is adjustable along an arm support axis, which is preferably dominated by z-axis movement with a y-axis element; the knee support 1660 is adjustable along a knee support axis 1662, which is preferably dominated by y-axis movement with a z-axis element; and the foot support 1670 is adjustable along a foot support axis, which is preferably dominated by y-axis movement with a z-axis element.

If the patient is not facing the incoming proton beam, then the description of movements of support elements along the axes change, but the immobilization elements are the same.

Still referring to FIG. 16, the patient is preferably positioned on a patient positioning unit 1610, which optionally includes a bottom unit 1612 and a top unit 1614. The bottom unit is optionally a patient support platform or is attached to a patient support platform 1618. Preferably, some of the patient positioning constraints 1615 are fixed to and supported by the patient positioning unit 1610. For instance, some of the patient positioning constraints 1615 are fixed to and supported by the bottom unit 1612 and some of the patient positioning constraints 1615 are fixed to and supported by the top unit 1614. Additionally, preferably the patient positioning unit 1610 is adjustable along the y-axis 1616 to allow vertical positioning of the patient relative to the proton therapy beam 260. Additionally, preferably the patient positioning unit 1610 is rotatable about a rotation axis 1617, such as about the y-axis, to allow rotational control and positioning of the patient relative to the proton beam path 260. The rotation of the positioning unit is illustrated about the rotation axis 1617 at three distinct times, $t_1$, $t_2$, and $t_3$. Any of the positioning embodiments described herein are optionally rotatable about eh rotation or y-axis.

Still referring to FIG. 16, an optional camera 1680 is illustrated. The camera views the subject 1530 creating an video image. The image is provided to one or more operators of the charged particle beam system and allows the operators a safety mechanism for determining if the subject has moved or desires to terminate the proton therapy treatment procedure. Based on the video image, the operators may suspend or terminate the proton therapy procedure. For example, if the operator observes via the video image that the subject is moving, then the operator has the option to terminate or suspend the proton therapy procedure.

Still referring to FIG. 16, an optional video display 1690 is provided to the patient. The video display optionally presents to the patient any of: operator instructions, system instructions, status of treatment, or entertainment.

Motors for positioning the constraints 1615, the camera 1680, and video display 1690 are preferably mounted above or below the proton path 269.

Respiration control is optionally performed by using the video display 1690. As the patient breathes, internal and external structures of the body move in both absolute terms and in relative terms. For example, the outside of the chest cavity and internal organs both have absolute moves with a breath. In addition, the relative position of an internal organ relative to another body component, such as an outer region of the body, a bone, support structure, or another organ, moves with each breath. Hence, for more accurate and precise tumor targeting, the proton beam is preferably delivered at point a in time where the position of the internal structure or tumor is well defined, such as at the top and/or bottom of each breath. The video display 1690 is used to help coordinate the proton beam delivery with the patient's respiration cycle. For example, the video display 1690 optionally displays to the patient a command, such as a hold breath statement, a breath statement, a countdown indicating when a breath will next need to be held, or a countdown until breathing may resume.

Sitting Patient Positioning/Immobilization

In a second partial immobilization embodiment, the patient is partially restrained in a seated position. The sitting restraint system has support structures that are similar to the support structures used in the semi-vertical positioning system, described supra with the exception that the seat support 1620 is replaced by a chair and the knee support 1660 is not required. The seated restraint system generally retains the adjustable support, rotation about the y-axis, camera, video, and respiration control parameters described in the semi-vertical embodiment, described supra.

Figure 17:
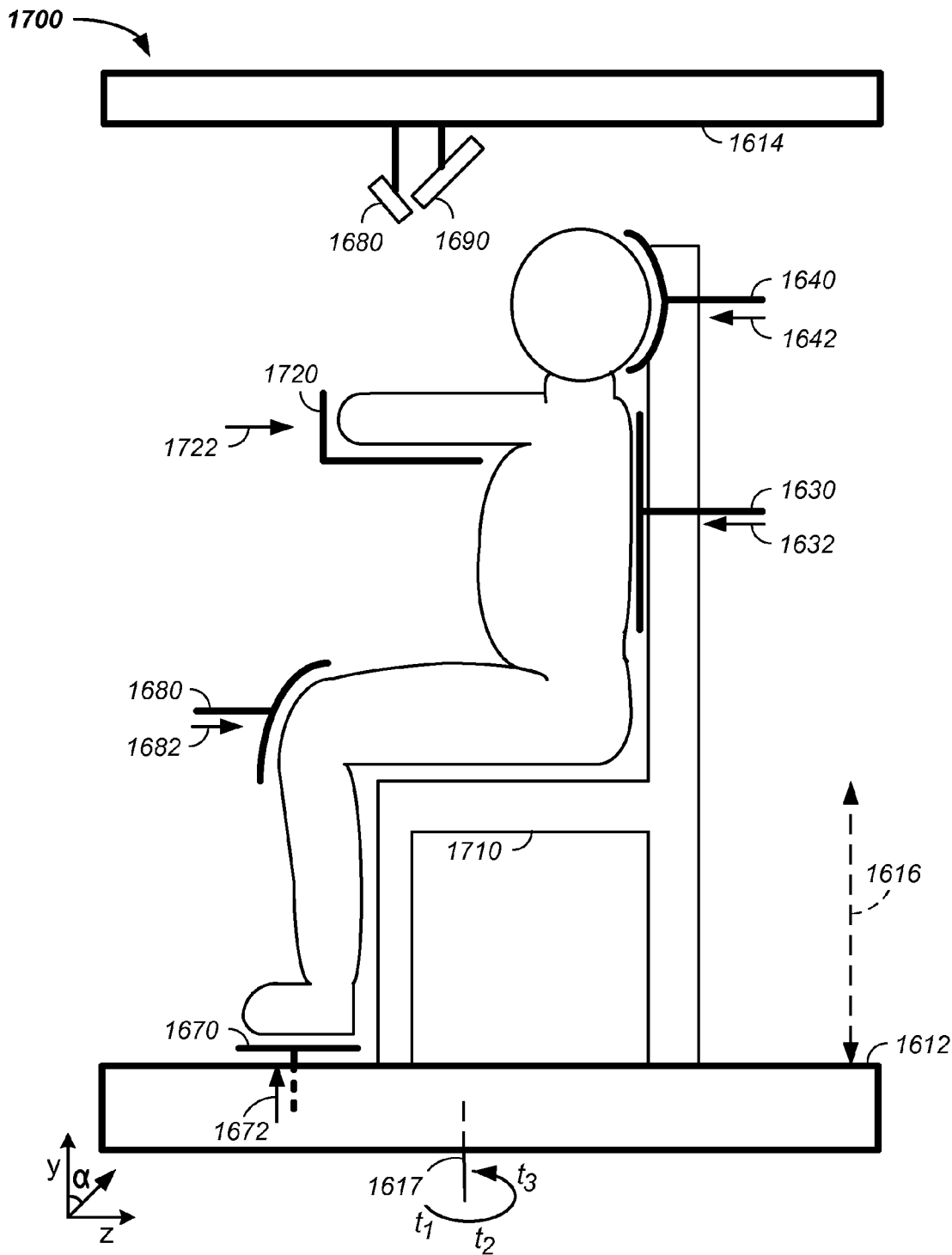
FIG. 17 illustrates a seated positioning system.

Referring now to FIG. 17, a particular example of a sitting patient semi-immobilization system 1700 is provided. The sitting system 1700 is preferably used for treatment of head and neck tumors. As illustrated, the patient is positioned in a seated position on a chair 1710 for particle therapy. The patient is further immobilized using any of the: the head support 1640, the back support 1630, a hand support 1720, the knee support 1660, and the foot support 1670. The supports 1640, 1630, 1720, 1660, 1670 preferably have respective axes of adjustment 1642, 1632, 1722, 1662, 1672 as illustrated. The chair 1710 is either readily removed to allow for use of a different patient constraint system or adapts to a new patient position, such as the semi-vertical system 1600.

Laying Patient Positioning/Immobilization

In a third partial immobilization embodiment, the patient is partially restrained in a laying position. The laying restraint system has support structures that are similar to the support structures used in the sitting positioning system 1700 and semi-vertical positioning system 1600, described supra. In the laying position, optional restraint, support, or partial immobilization elements include one or more of: the head support 1640 and the back, hip, and shoulder support 1630. The supports 1640, 1630 preferably have respective axes of adjustment 1642, 1632 that are rotated as appropriate for a laying position of the patient. The laying position restraint system generally retains the adjustable supports, rotation about the y-axis, camera, video, and breath control parameters described in the semi-vertical embodiment, described supra.

If the patient is very sick, such as the patient has trouble standing for a period of about one to three minutes required for treatment, then being in a partially supported system can result in some movement of the patient due to muscle strain. In this and similar situations, treatment of a patient in a laying position on a support table is preferentially used. The support table has a horizontal platform to support the bulk of the weight of the patient. Preferably, the horizontal platform is detachable from a treatment platform Additionally, leg support elements 1840 moveably along a leg support axis or arc 1842 and/or arm support elements 1850 movable along an arm support arc 1852 are optionally added to raise, respectively, an arm or leg out of the proton beam path 269 for treatment of a tumor in the torso or to move an arm or leg into the proton beam path 269 for treatment of a tumor in the arm or leg. This increases proton delivery efficiency, as described infra.

Figure 18:
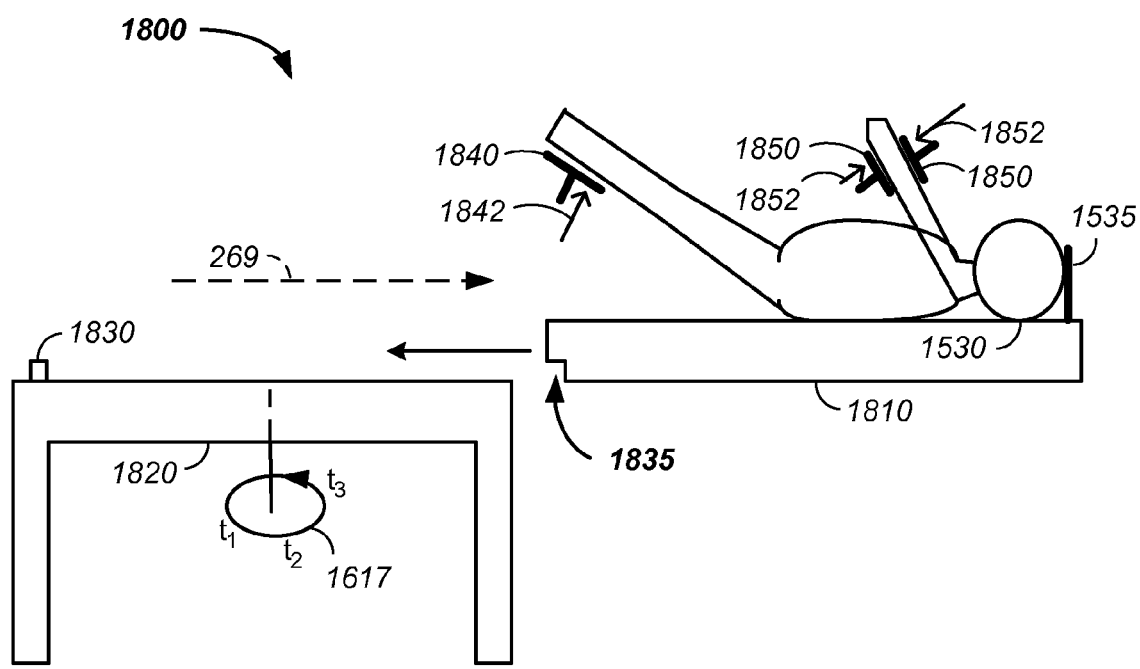
FIG. 18 illustrates a laying positioning system.

Referring now to FIG. 18, in a laying positioning system 1800 the patient 1530 is positioned on a platform 1610, which has a substantially horizontal portion for supporting the weight of the body in a horizontal position. For clarity of presentation, the head support 1640 and back support 1630 elements, though preferably present, are not illustrated. Similarly, optional hand grips 2110, 2120, though preferably used, are not illustrated for clarity. The hand grips are described infra. One or more leg support 1840 elements are used to position the patient's leg. A leg support 1840 element is preferably adjustable along at least one leg adjustment axis 1842 or along an arc to position the leg into the proton beam path 269 or to remove the leg from the proton beam path 269, as described infra. An arm support 1850 element is preferably adjustable along at least one arm adjustment axis 1850 or along an arc to position the arm into the proton beam path 269 or to remove the arm from the proton beam path 269, as described infra. Both the leg support 1840 and arm support 1850 elements are optional.

Preferably, the patient is positioned on the platform 1610 in an area or room outside of the proton beam path 269 and is wheeled or slid into the treatment room or proton beam path area. For example, the patient is wheeled into the treatment room on a gurney where the top of the gurney, which is the platform 1610, detaches and is positioned onto a table 1620. The platform 1610 is preferably lifted onto the table 1620 or slid onto the table 1620. In this manner, the gurney or bed need not be lifted onto the table 1620.

The semi-vertical patient positioning system 1600 and sitting patient positioning system 1700 are preferentially used to treatment of tumors in the head or torso due to efficiency. The semi-vertical patient positioning system 1600, sitting patient positioning system 1700, and laying patient positioning system 1800 are all usable for treatment of tumors in the patient's limbs.

Support System Elements

Positioning constraints 1615 include all elements used to position the patient, such as those described in the semi-vertical positioning system 1600, sitting positioning system 1700, and laying positioning system 1800. Preferably, positioning constraints 1615 or support system elements are aligned in positions that do not impede or overlap the proton beam path 269. However, in some instances the positioning constraints 1615 are in the proton beam path 269 during at least part of the time of treatment of the patient. For instance, a positioning constraint 1615 element may reside in the proton beam path 269 during part of a time period where the patient is rotated about the y-axis during treatment. In cases or time periods that the positioning constraints 1615 or support system elements are in the proton beam path, then an upward adjustment of proton beam energy is preferably applied that increases the proton beam energy to offset the positioning constraint 1615 element impedance of the proton beam. In one case, the proton beam energy is increased by a separate measure of the positioning constraint 1615 element impedance determined during a reference scan of the positioning constraint 1615 system element or set of reference scans of the positioning constraint 1615 element as a function of rotation about the y-axis.

For clarity, the positioning constraints 1615 or support system elements are herein described relative to the semi-vertical positioning system 1600; however, the positioning elements and descriptive x-, y-, and z-axes are adjustable to fit any coordinate system, to the sitting positioning system 1700, or the laying positioning system 1800.

Figure 19:
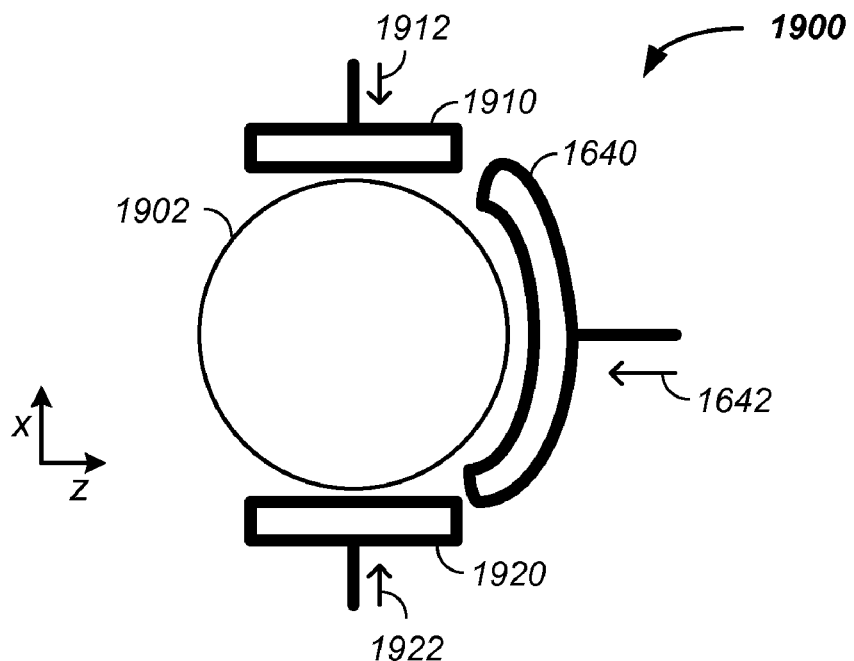
FIG. 19 illustrates a head restraint system.

Referring now to FIG. 19 an example of a head support system 1900 is described to support, align, and/or restrict movement of a human head 1902. The head support system 1900 preferably has several head support elements including any of: a back of head support 1640, a right of head alignment element 1910, and a left of head alignment element 1920. The back of head support element is preferably curved to fit the head and is optionally adjustable along a head support axis 1642, such as along the z-axis. Further, the head supports 1640, like the other patient positioning constraints 1615, is preferably made of a semi-rigid material, such as a low or high density foam, and has an optional covering, such as a plastic or leather. The right of head alignment element 1910 and left of head alignment elements 1920 or head alignment elements 1910, 1920, are primarily used to semi-constrain movement of the head. The head alignment elements are preferably padded and flat, but optionally have a radius of curvature to fit the side of the head. The right 1910 and left 1920 head alignment elements are preferably respectively movable along translation axes 1912, 1922 to make contact with the sides of the head. Restricted movement of the head during proton therapy is important when targeting and treating tumors in the head or neck. The head alignment elements 1910, 1920 and the back of head support element 1640 combine to restrict tilt, rotation or yaw, roll and/or position of the head in the x-, y-, z-axes coordinate system.

Figure 20:
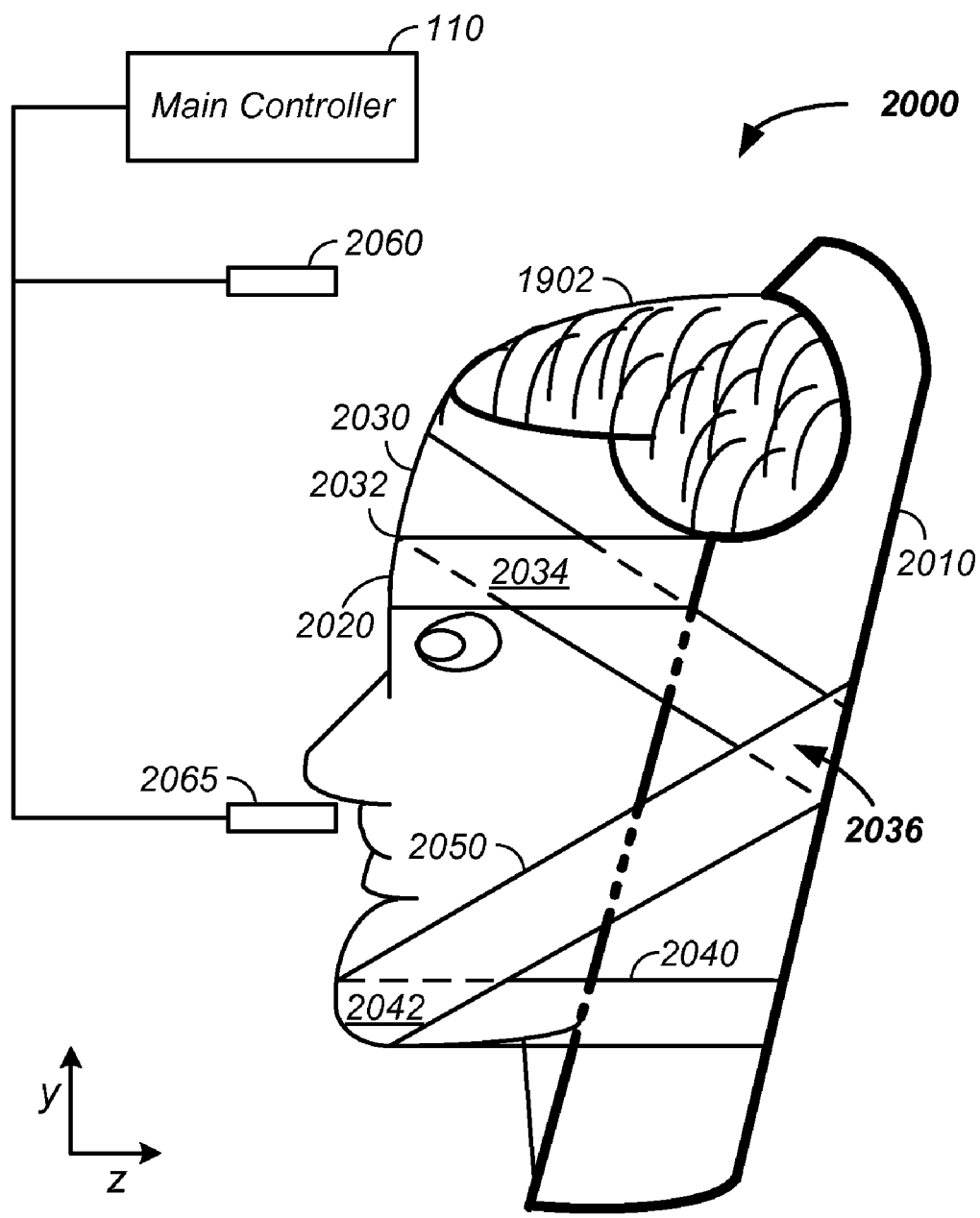
FIG. 20 illustrates a head restraint system.

Referring now to FIG. 20 another example of a head support system 2000 is described for positioning and/or restricting movement of a human head 1902 during proton therapy of a solid tumor in the head or neck. In this system, the head is restrained using 1, 2, 3, 4, or more straps or belts, which are preferably connected or replaceably connected to a back of head support element 2010. In the example illustrated, a first strap 2020 pulls or positions the forehead to the support element 2010, such as by running predominantly along the z-axis. Preferably a second strap 2030 works in conjunction with the first strap 2020 to prevent the head from undergoing tilt, yaw, roll or moving in terms of translational movement on the x-, y-, and z-axes coordinate system. The second strap 2030 is preferably attached or replaceable attached to the first strap 2020 at or about: (1) the forehead 2032; (2) on one or both sides of the head; and/or (3) at or about the support element 2010. A third strap 2040 preferably orientates the chin of the subject relative to the support element 2010 by running dominantly along the z-axis. A fourth strap 2050 preferably runs along a predominantly y- and z-axes to hold the chin relative to the head support element 2010 and/or proton beam path. The third 2040 strap preferably is attached to or is replaceably attached to the fourth strap 2050 during use at or about the patient's chin 2042. The second strap 2030 optionally connects to the fourth strap 2050 at the rear of the head 2036, such as at or about the support element 2010. The four straps 2020, 2030, 2040, 2050 are illustrative in pathway and interconnection. Any of the straps optionally hold the head along different paths around the head and connect to each other in separate fashion. Naturally, a given strap preferably runs around the head and not just on one side of the head. Any of the straps 2020, 2030, 2040, and 2050 are optionally used independently or in combinations or permutations with the other straps. The straps are optionally indirectly connected to each other via a support element, such as the head support element 2010. The straps are optionally attached to the support element 2010 using hook and loop technology, a buckle, or fastener. Generally, the straps combine to control position, front-to-back movement of the head, side-to-side movement of the head, tilt, yaw, roll, and/or translational position of the head.

The straps are preferably of known impedence to proton transmission allowing a calculation of peak energy release along the z-axis to be calculated, such as an adjustment to the Bragg peak is made based on the slowing tendency of the straps to proton transport.

Figure 21:
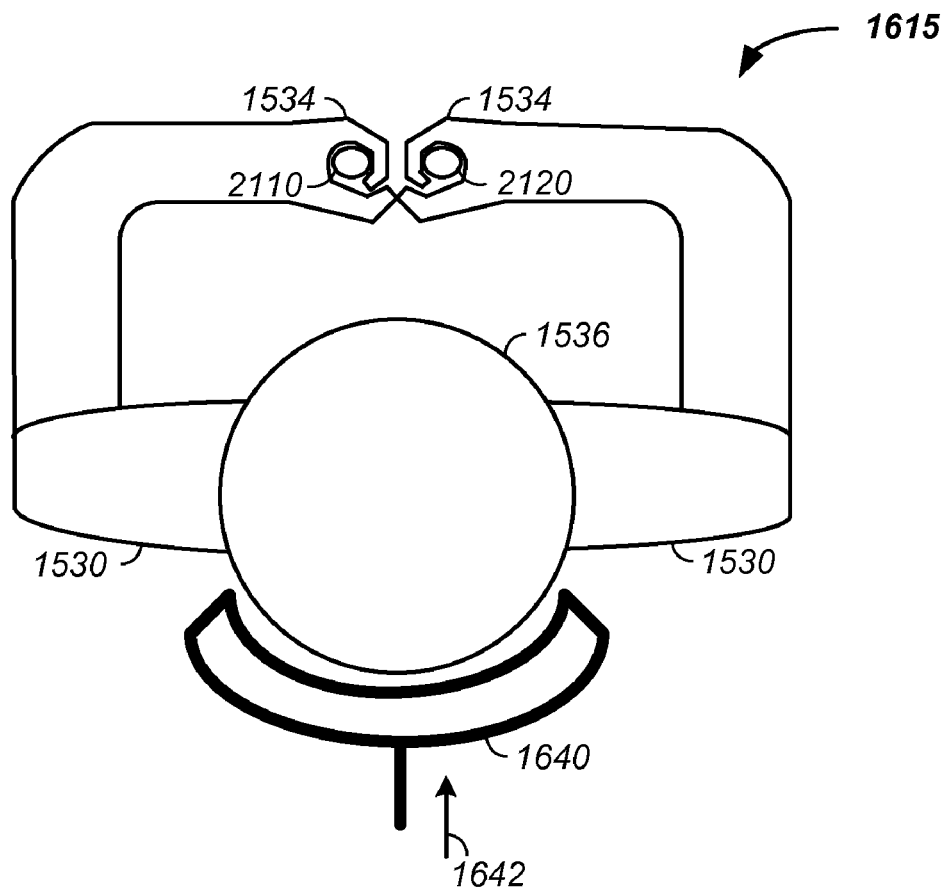
FIG. 21 illustrates hand and head supports.

Referring now to FIG. 21, still another example of a head support 1640 is described. The head support 1640 is preferably curved to fit a standard or child sized head. The head support 1640 is optionally adjustable along a head support axis 1642. Further, the head supports 1640, like the other patient positioning constraints 1615, is preferably made of a semi-rigid material, such as a low or high density foam, and has an optional covering, such as a plastic or leather.

Elements of the above described head support, head positioning, and head immobilization systems are optionally used separately or in combination.

Still referring to FIG. 21, an example of the arm support 1650 is further described. The arm support preferably has a left hand grip 2110 and a right hand grip 2120 used for aligning the upper body of the patient 1530 through the action of the patient 1530 gripping the left and right hand grips 2010, 2020 with the patient's hands 1534. The left and right hand grips 2110, 2120 are preferably connected to the arm support 1650 that supports the mass of the patient's arms. The left and right hand grips 2110, 2120 are preferably constructed using a semi-rigid material. The left and right hand grips 2110, 2120 are optionally molded to the patient's hands to aid in alignment. The left and right hand grips optionally have electrodes, as described supra.

Figure 22:
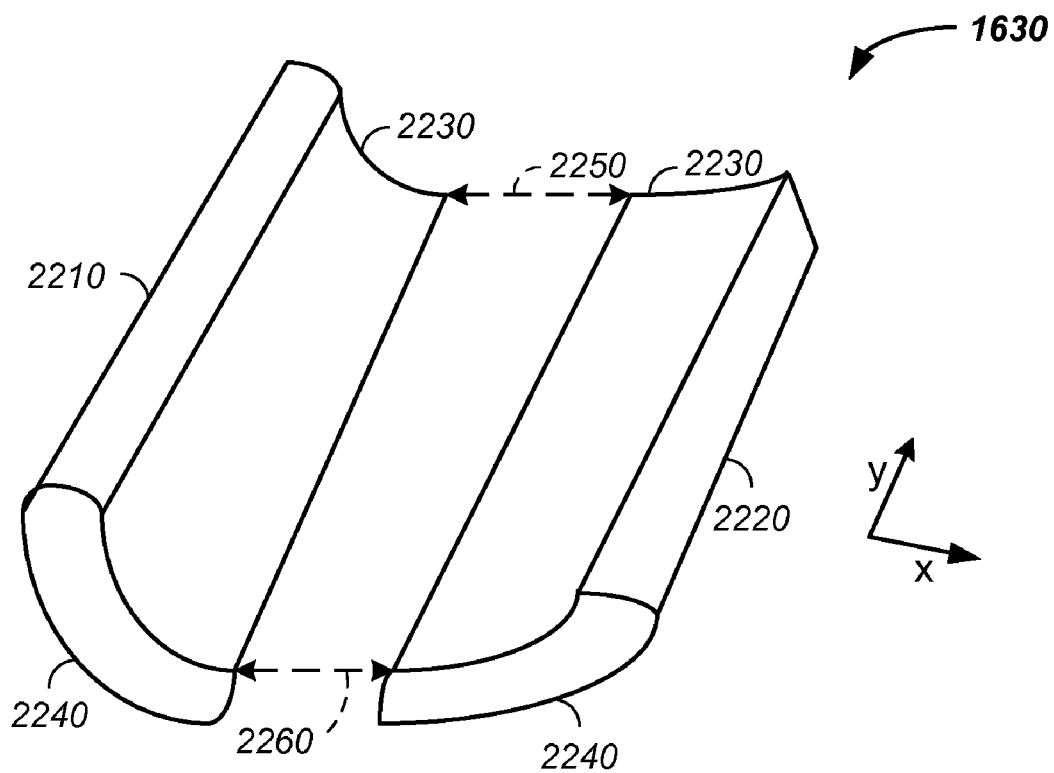
FIG. 22 illustrates a back support.

Referring now to FIG. 22, an example of the back support 1630 is further described. Referring to FIG. 22, an example of a perspective orientation of the back support 1630 is illustrated. The back support is preferably curved to support the patient's back and to wrap onto the sides of the patient's torso. The back support preferably has two semi-rigid portions, a left side 2210 and right side 2220. Further, the back support 1630 has a top end 2230 and a bottom end 2240. A first distance 2250 between the top ends 2230 of the left side 2210 and right side 2220 is preferably adjustable to fit the upper portion of the patient's back. A second distance 2260 between the bottom ends 2240 of the left side 2210 and right side 2220 is preferably independently adjustable to fit the lower portion of the patient's back.

Figure 23:
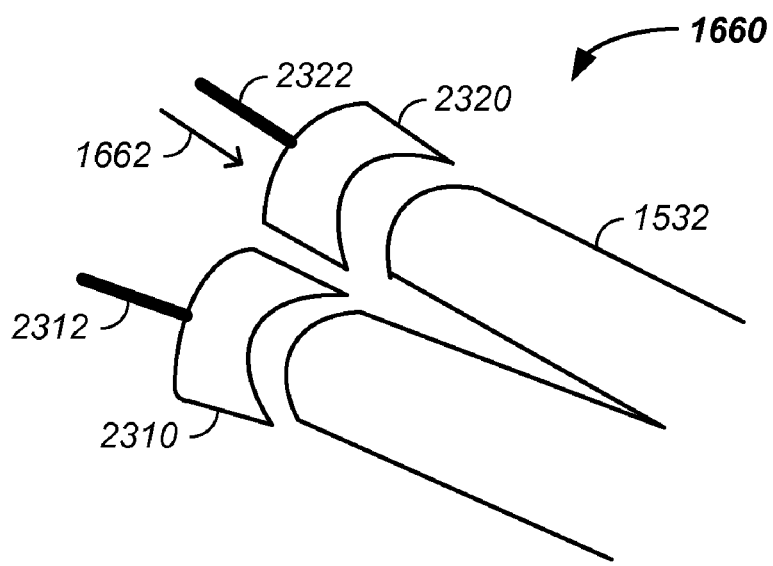
FIG. 23 illustrates a knee support.

Referring now to FIG. 23, an example of the knee support 1660 is further described. The knee support preferably has a left knee support 2310 and a right knee support 2320 that are optionally connected or individually movable. Both the left and right knee supports 2310, 2320 are preferably curved to fit standard sized knees 1532. The left knee support 2310 is optionally adjustable along a left knee support axis 2312 and the right knee support 2320 is optionally adjustable along a right knee support axis 2322. Alternatively, the left and right knee supports 2310, 2320 are connected and movable along the knee support axis 1662. Both the left and right knee supports 2310, 2320, like the other patient positioning constraints 1615, are preferably made of a semi-rigid material, such as a low or high density foam, having an optional covering, such as a plastic or leather.

Positioning System Computer Control

One or more of the patient positioning unit 1610 components and/or one or more of the patient positioning constraints 1615 are preferably under computer control, where the computer control positioning devices, such as via a series of motors and drives, to reproducibly position the patient. For example, the patient is initially positioned and constrained by the patient positioning constraints 1615. The position of each of the patient positioning constraints 1615 is recorded and saved by the main controller 110, by a sub-controller or the main controller 110, or by a separate computer controller. Then, medical devices are used to locate the tumor 1520 in the patient 1530 while the patient is in the orientation of final treatment. The imaging system 170 includes one or more of: MRI's, X-rays, CT's, proton beam tomography, and the like. Time optionally passes at this point where images from the imaging system 170 are analyzed and a proton therapy treatment plan is devised. The patient may exit the constraint system during this time period, which may be minutes, hours, or days. Upon return of the patient to the patient positioning unit 1610, the computer can return the patient positioning constraints 1615 to the recorded positions. This system allows for rapid repositioning of the patient to the position used during imaging and development of the treatment plan, which minimizes setup time of patient positioning and maximizes time that the charged particle beam system 100 is used for cancer treatment.

Proton Delivery Efficiency

A Bragg peak energy profile shows that protons deliver their energy across the entire length of the body penetrated by the proton up to a maximum penetration depth. As a result, energy is being delivered to healthy tissue, bone, and other body constituents before the proton beam hits the tumor. It follows that the shorter the pathlength in the body prior to the tumor, the higher the efficiency of proton delivery efficiency, where proton delivery efficiency is a measure of how much energy is delivered to the tumor relative to healthy portions of the patient. Examples of proton delivery efficiency include: (1) a ratio proton energy delivered the tumor and proton energy delivered to non-tumor tissue; (2) pathlength of protons in the tumor versus pathlength in the non-tumor tissue; and (3) damage to a tumor compared to damage to healthy body parts. Any of these measures are optionally weighted by damage to sensitive tissue, such as a nervous system element, heart, brain, or other organ. To illustrate, for a patient in a laying position where the patient is rotated about the y-axis during treatment, a tumor near the hear would at times be treated with protons running through the head-to-heart path, leg-to-heart path, or hip-to-heart path, which are all inefficient compared to a patient in a sitting or semi-vertical position where the protons are all delivered through a shorter chest-to-heart; side-of-body-to-heart, or back-to-heart path. Particularly, compared to a laying position, using a sitting or semi-vertical position of the patient, a shorter pathlength through the body to a tumor is provided to a tumor located in the torso or head, which is a higher or better proton delivery efficiency.

Herein proton delivery efficiency is separately described from the time efficiency or synchrotron use efficiency, which is a fraction of time that the charged particle beam apparatus is in operation.

Patient Placement

Preferably, the patient 1530 is aligned in the proton beam path 269 in a precise and accurate manner. Several placement systems are described. The patient placement systems are described using the laying positioning system 1800, but are equally applicable to the semi-vertical 1600 and sitting 1700 positioning systems.

In a first placement system, the patient 1530 is positioned in a known location relative to the platform 1810. For example, one or more of the positioning constraints 1615 position the patient 1530 in a precise and/or accurate location on the platform 1810. Optionally, a placement constraint element 1535 connected or replaceably connected to the platform 1810 is used to position the patient on the platform. The placement constraint element(s) is used to position any position of the patient, such as a hand, limb, head, or torso element.

In a second placement system, one or more positioning constraints 1615 or support element, such as the platform 1810, is aligned versus an element in the patient treatment room. Essentially a lock and key system is optionally used, where a lock 1830 fits a key 1835. The lock and key elements combine to locate the patient relative to the proton beam path 269 in terms of any of the x-, y-, and z-position, tilt, yaw, and roll. Essentially the lock is a first registration element and the key is a second registration element fitting into, adjacent to, or with the first registration element to fix the patient location and/or a support element location relative to the proton beam path 269. Examples of a registration element include any of a mechanical element, such as a mechanical stop, and an electrical connection indicating relative position or contact.

In a third placement system, the imaging system, described supra, is used to determine where the patient is relative to the proton beam path 269 or relative to an imaging marker 1860 placed in an support element or structure holding the patient, such as in the platform 1810. When using the imaging system, such as an X-ray imaging system, then the first placement system or positioning constraints 1615 minimize patient movement once the imaging system determines location of the subject. Similarly, when using the imaging system, such as an X-ray imaging system, then the first placement system and/or second positioning system provide a crude position of the patient relative to the proton beam path 269 and the imaging system subsequently determines a fine position of the patient relative to the proton beam path 269.

Monitoring Respiration

Preferably, the patient's respiration cycle or breathing pattern is monitored. When a subject, also referred to herein as a patient, is breathing many portions of the body move with each breath. For example, when a subject breathes the lungs move as do relative positions of organs within the body, such as the stomach, kidneys, liver, chest muscles, skin, heart, and lungs. Generally, most or all parts of the torso move with each breath. Indeed, the inventors have recognized that in addition to motion of the torso with each breath, various motion also exists in the head and limbs with each breath. Motion is to be considered in delivery of a proton dose to the body as the protons are preferentially delivered to the tumor and not to surrounding tissue. Motion thus results in an ambiguity in where the tumor resides relative to the beam path. To partially overcome this concern, protons are preferentially delivered at the same point in each of a series of respiration cycles.

Initially a rhythmic pattern of respiration of a subject is determined. The cycle is observed or measured. For example, a proton beam operator can observe when a subject is breathing or is between breaths and can time the delivery of the protons to a given period of each breath. Alternatively, the subject is told to inhale, exhale, and/or hold their breath and the protons are delivered during the commanded time period.

Preferably, one or more sensors are used to determine the respiration cycle of the individual. Two examples of a respiration monitoring system are provided: (1) a thermal monitoring system and (2) a force monitoring system.

Referring again to FIG. 20, an example of the thermal respiration monitoring system is provided 2000. In the thermal respiration monitoring system, a sensor is placed by the nose and/or mouth of the patient. As the jaw of the patient is optionally constrained, as described supra, the thermal breath monitoring system is preferably placed by the patient's nose exhalation path. To avoid steric interference of the thermal sensor system components with proton therapy, the thermal respiration monitoring system is preferably used when treating a tumor not located in the head or neck, such as a when treating a tumor in the torso or limbs. In the thermal monitoring system, a first thermal resistor 2065 is used to monitor the patient's respiration cycle and/or position in time in the patient's respiration cycle. Preferably, the first thermal resistor 2065 is placed by the patient's nose, such that the patient exhaling through their nose onto the first thermal resistor 2065 warms the first thermal resistor 2065 indicating an exhale. Preferably, a second thermal resistor 2060 operates as an environmental temperature sensor. The second thermal resistor 2060 is preferably placed out of the exhalation path of the patient but in the same local room environment as the first thermal resistor 2065. Generated signal, such as current from the thermal resistors 2065, 2060, is preferably converted to voltage and communicated with the main controller 110 or a sub-controller of the main controller. Preferably, the second thermal resistor 2060 is used to adjust for the environmental temperature fluctuation that is part of a signal of the first thermal resistor 2065, such as by calculating a difference between the values of the thermal resistors 2065, 2060 to yield a more accurate reading of the patient's respiration cycle.

Referring again to FIG. 17, an example of the force/pressure respiration monitoring system is provided. In the force breath monitoring system, a sensor is placed by the torso. To avoid steric interference of the force sensor system components with proton therapy, the force breath monitoring system is preferably used when treating a tumor located in the head, neck or limbs. In the force monitoring system, a belt or strap 1730 is placed around an area of the patient's torso that expands and contracts with each breath cycle of the patient. The belt 1730 is preferably tight about the patient's chest and is flexible. A force meter 1732 is attached to the belt and senses the patients breathing pattern. The forces applied to the force meter 1732 correlate with periods of the breathing cycle. The signals from the force meter 1732 are preferably communicated with the main controller 110 or a sub-controller of the main controller. The sensor preferably provides a continuous or semi-continuous measure of the patient's respiration cycle or breathing pattern. While the length of each breath may vary, the sensor readout contains patterns or chemometrically and/or statistically defined shapes indicative of stages of respiration, such as full inhalation, full exhalation, a rate of change of air intake or outtake, magnitude of the respiration, and phase of the respiration. Based on the shape elements, predictions are optionally made as to timing of future stages of respiration so that commands may be issued to the patient that are readily achieved with preferably minor effort.

Respiration Control

Once the rhythmic pattern of the subject's respiration pattern is determined, a signal is optionally delivered to the subject to more precisely control the respiration frequency. For example, a display screen is placed in front of the subject directing the subject when to hold their breath and when to breath. Typically, a respiration control module uses input from one or more of the respiration sensors. For example, the input is used to determine when the next breath exhale is to complete. At the bottom of the breath, the control module displays a hold breath signal to the subject, such as on a monitor, via an oral signal, digitized and automatically generated voice command, or via a visual control signal. Preferably, a display monitor is positioned in front of the subject and the display monitor displays at least breathing commands to the subject. Typically, the subject is directed to hold their breath for a short period of time, such as about one-half, one, two, or three seconds. The period of time the subject is asked to hold their breath is less than about ten seconds and preferably less than about three to five seconds. The period of time the breath is held is preferably synchronized to the delivery time of the proton beam to the tumor, which is about one-half, one, two, or three seconds. While delivery of the protons at the bottom of the breath is preferred, protons are optionally delivered at any point in the breathing cycle, such as upon full inhalation. Delivery at the top of the breath or when the patient is directed to inhale deeply and hold their breath by the respiration control module is optionally performed as at the top of the breath the chest cavity is largest and for some tumors the distance between the tumor and surrounding tissue is maximized or the surrounding tissue is rarefied as a result of the increased volume. Hence, protons hitting surrounding tissue is minimized. Optionally, the display screen tells the subject when they are about to be asked to hold their breath, such as with a 3, 2, 1, second countdown so that the subject is aware of the task they are about to be asked to perform.

Proton Beam Therapy Synchronization with Respiration

A proton delivery control algorithm is used to synchronize delivery of the protons to the tumor within a given period of each breath, such as at the top or bottom of a breath when the subject is holding their breath. The proton delivery control algorithm is preferably integrated with the respiration control module. Thus, the proton delivery control algorithm knows when the subject is breathing, where in the respiration cycle the subject is, and/or when the subject is holding their breath. The proton delivery control algorithm controls when protons are injected and/or inflected into the synchrotron, when an RF signal is applied to induce an oscillation, as described supra, and when a DC voltage is applied to extract protons from the synchrotron, as described supra. Typically, the proton delivery control algorithm initiates proton inflection and subsequent RF induced oscillation before the subject is directed to hold their breath or before the identified period of the respiration cycle selected for a proton delivery time. In this manner, the proton delivery control algorithm can deliver protons at a selected period of the respiration cycle by simultaneously or nearly simultaneously delivering the high DC voltage to the second pair of plates, described supra, which results in extraction of the protons from the synchrotron and subsequent delivery to the subject at the selected time point. Since the period of acceleration of protons in the synchrotron is constant or known for a desired energy level of the proton beam, the proton delivery control algorithm is used to set an AC RF signal that matches the respiration cycle or directed respiration cycle of the subject.

Multi-Field Illumination

The 3-dimensional scanning system of the proton spot focal point, described supra, is preferably combined with a rotation/raster method. The method includes layer wise tumor irradiation from many directions. During a given irradiation slice, the proton beam energy is continuously changed according to the tissue's density in front of the tumor to result in the beam stopping point, defined by the Bragg peak, to always be inside the tumor and inside the irradiated slice. The novel method allows for irradiation from many directions, referred to herein as multi-field irradiation, to achieve the maximal effective dose at the tumor level while simultaneously significantly reducing possible side-effects on the surrounding healthy tissues in comparison with existing methods. Essentially, the multi-field irradiation system distributes dose-distribution at tissue depths not yet reaching the tumor.

Several examples are provided to further illustrate various embodiments of the charged particle therapy tumor treatment system.

In one example, a method and/or apparatus is used for controlling extraction of charged particles from a synchrotron based on a variable respiration rate of a patient. The system preferably includes a respiration sensor generating a respiration signal corresponding to a breathing pattern of the patient and a charged particle controller configured to dynamically adjust timing of extraction of the charged particles to occur in synchronization with the breathing pattern of the patient where the breathing pattern includes a changing respiration rate. Preferably, the systems operates over a sequential series of patient breaths where a time period of each individual breath is varied. Stated again, the system times delivery of the charged particles from the synchrotron based upon the changing respiration rate of the patient rather that on controlling the respiration of the patient.

In another example, a method and/or apparatus is used to control respiration of a patient during irradiation therapy of a tumor with charged particles from a charged particle cancer therapy system. Preferably, the system includes: a synchrotron configured to accelerate the charged particles, a respiration sensor generating a respiration signal corresponding to a breathing pattern of the patient, a respiration command controller using the respiration signal to determine at least one command, and a display screen configured to instruct the respiration of the patient with the command while the patient is positioned for irradiation therapy. Typically, the system uses the respiration signal to deliver the charged particles to the tumor in the seconds following display of the command on the display screen. Preferably, a charged particle controller controls timing of delivery of the charged particles to the tumor during a repeating period of the breathing pattern, where the timing includes timing injection of the charged particles into the synchrotron, timing of acceleration of the charged particles in the synchrotron, and/or timing of extraction of the charged particles from the synchrotron. Optionally, the timing controls timing of the charged particles from the synchrotron at non-periodic intervals correlating with non-periodic intervals of the patient's breathing pattern.

In still another example, a method and/or apparatus is used for controlling extraction of charged particles from a synchrotron for irradiation therapy of a tumor of a patient. the system preferably includes: a synchrotron configured to accelerate the charged particles, a respiration sensor generating a respiration signal corresponding to a variable rate breathing pattern of the patient, and a controller timing extraction of the charged particles to the tumor based on the variable breathing pattern, such as where the breathing pattern of the patient varies from breath to breath by about 0.1, 0.2, 0.5, 1, or 2 seconds.

In yet another example, the charged particle cancer therapy system includes control of any of:
- injection of hydrogen gas into an ion beam generation system, where a magnetic field barrier in the ion beam generation system exists between a high temperature plasma region and a low temperature plasma zone;
- an ion beam generation system including a first vacuum chamber on a first side of a converting foil and a second vacuum chamber on a second side of the converting foil, where the first vacuum operates at a separate pressure from the second vacuum chamber;
- an ion beam focusing system having conductive paths running across a negative ion beam path and a focusing electrode circumferentially surrounding the negative ion beam path, where electric field lines run between the focusing electrode and the metal conductive paths, where negative ions in the negative ion beam focus through force vectors running up the electric field lines during use, and where the negative ion beam is converted into the charge particles at a converting foil.

Preferably, timing includes multi-axis control of all of: negative ion generation, negative ion extraction and conversion to the charged particles, acceleration of the charged particles, extraction of the charged particles, and delivery position of the charged particles to the tumor.

Any of the examples provided herein are optionally operable with any of the method, apparatus, and/or system elements described herein.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for controlling extraction of charged particles from a synchrotron for irradiation therapy of a tumor of a patient, comprising:
   a synchrotron configured to accelerate the charged particles, said synchrotron comprising:
      a radio-frequency cavity system comprising a first pair of blades for inducing oscillation of the charged particles; and
      a foil configured to yield slowed charged particles from the charged particles having sufficient oscillation to traverse said foil, wherein the slowed charged particles pass through a second pair of blades having an extraction voltage directing the charged particles out of said synchrotron through a Lamberson extraction magnet, said radio-frequency cavity system for inducing oscillation configured and timed using said respiration signal;
   a respiration sensor generating a respiration signal, said respiration signal corresponding to a variable rate breathing pattern of the patient, said respiration sensor comprising at least one of:
      a force meter strapped to the patient's chest;
      a first thermal resistor configured in a first position proximate an exhalation path of the patient; and
      a second thermal resistor configured in a second position both out of the exhalation path of the patient and in a local room environment common with the patient, wherein said respiration signal is generated using differences between readings from said first thermal resistor and said second thermal resistor,
   wherein said radio-frequency cavity system for inducing oscillation is timed using said respiration signal to time extraction of the charged particles to the tumor based on said variable rate breathing pattern.

2. The apparatus of claim 1, further comprising:
   a charged particle controller controlling delivery of the charged particles from the synchrotron at sequential non-periodic intervals, said non-periodic intervals correlating with said variable rate breathing pattern, wherein said breathing pattern comprises sequential respiration cycles varying by at least one second in length.

3. The apparatus of claim 1, further comprising:
   an X-ray generation source configured to generate X-rays of the patient and the tumor at said non-periodic intervals.

* * * * *